(12) United States Patent
Cockerill et al.

(10) Patent No.: US 10,406,166 B2
(45) Date of Patent: Sep. 10, 2019

(54) ANTIMICROBIAL COMPOUND

(71) Applicant: The University of Durham, Durham (GB)

(72) Inventors: Stuart Cockerill, Durham (GB); Jonathan Harburn, Durham (GB)

(73) Assignee: The University of Durham, Durham (GB)

( * ) Notice: Subject to any disclaimer, the term of this patent is extended or adjusted under 35 U.S.C. 154(b) by 0 days.

(21) Appl. No.: 15/566,183

(22) PCT Filed: Apr. 15, 2016

(86) PCT No.: PCT/GB2016/051053
§ 371 (c)(1),
(2) Date: Oct. 12, 2017

(87) PCT Pub. No.: WO2016/166546
PCT Pub. Date: Oct. 20, 2016

(65) Prior Publication Data
US 2018/0085378 A1 Mar. 29, 2018

(30) Foreign Application Priority Data
Apr. 16, 2015 (GB) .................................. 1506448.8

(51) Int. Cl.
| C07D 401/12 | (2006.01) |
| C07D 403/12 | (2006.01) |
| C07D 413/14 | (2006.01) |
| A61K 31/5513 | (2006.01) |
| A61P 31/04 | (2006.01) |
| A61P 31/14 | (2006.01) |
| A61P 31/16 | (2006.01) |
| A61K 31/4427 | (2006.01) |
| C07D 213/61 | (2006.01) |
| C07D 213/64 | (2006.01) |
| C07D 401/04 | (2006.01) |

(52) U.S. Cl.
CPC ...... *A61K 31/5513* (2013.01); *A61K 31/4427* (2013.01); *C07D 213/61* (2013.01); *C07D 213/64* (2013.01); *C07D 401/04* (2013.01); *C07D 401/12* (2013.01)

(58) Field of Classification Search
CPC .................................................. C07D 401/12
See application file for complete search history.

(56) References Cited

FOREIGN PATENT DOCUMENTS

| GB | 2259013 A | 8/1991 |
| WO | WO 2004026843 A1 | 4/2004 |
| WO | WO 2004106310 A1 | 12/2004 |
| WO | WO 2005089769 A1 | 9/2005 |
| WO | WO 2007/034127 A1 | 3/2007 |

*Primary Examiner* — Emily A Bernhardt
(74) *Attorney, Agent, or Firm* — Rudy J. Ng; Bozicevic, Field & Francis LLP

(57) ABSTRACT

The invention relates to compounds of formula (I), and pharmaceutical uses thereof. Particular aspects of the invention relate to methods of synthesizing the compounds and the use of those compounds in treating, ameliorating, or preventing a microbial infection.

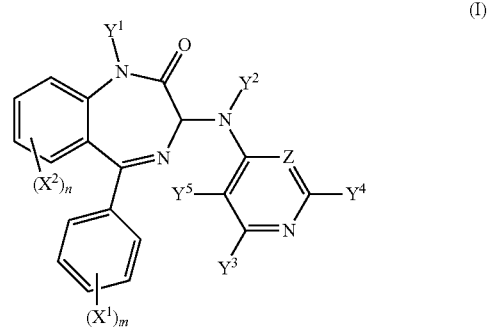

16 Claims, 13 Drawing Sheets

| Compound | Amino-Pyridine Ring A | | Amido- Pyridine Ring B | | |
|---|---|---|---|---|---|
| | 2,6-$F_2$ | 3,5-$F_2$ | 2,6-$F_2$ | 3,5-$F_2$ | |
| (3) | -93.61 | -163.97 | | | |
| (6) | -93.08 | -161.83 | -86.998 | -140.78 | -146.15 |
| (5) | -93.16 | -161.86 | | | |
| (11) | | | -86.34 | -141.42 | |
| (12) | | | -86.22 | -140.57 | |

| | | Minimum Inhibitory Concentration (mg/L) of 5-Phenyl-3-amino-2,3-dihydro-1H-1,4-benzodiazepin-2-one (5) | | | |
|---|---|---|---|---|---|
| | | 01.07.14 | | 08.07.14 | |
| | | 22h | 48h | 22h | 48h |
| Gram Positives | *Bacillus subtilis* NCTC 9372 | >128 | >128 | >32 | >32 |
| | *Listeria monocytogenes* NCTC 11994 | 16 | >128 | 16 | 16 |
| | *Staphylococci epidermidis* NCTC 11047 | 16 | 64 | 32 | >32 |
| | *Staphylococcus aureus* NCTC 6571 | 16 | 64 | 32 | >32 |
| | *Staphylococcus aureus* (MRSA) NCTC 11939 | 16 | 16 | 16 | 16 |
| | *Streptococcus pyogenes* NCTC 8306 | 64 | 64 | >32 | >32 |

Figure 13

Minimum Inhibitory Concentration (mg/L)

<table>
<tr><th rowspan="3"></th><th rowspan="3"></th><th colspan="4">5-Phenyl-3-amino-2,3-dihydro-1H-1,4-benzodiazepin-2-one</th><th colspan="4">5-Phenyl-R-3-[(tetrafluoropyridin-4-yl)amino]-2,3-dihydro-1H-1,4-benzodiazepin-2-one</th><th colspan="4">5-Phenyl-S-3-[(tetrafluoropyridin-4-yl)amino]-2,3-dihydro-1H-1,4-benzodiazepin-2-one</th></tr>
<tr><th colspan="2">01.07.14</th><th colspan="2">08.07.14</th><th colspan="2">16.09.14</th><th colspan="2">17.09.14</th><th colspan="2">16.09.14</th><th colspan="2">17.09.14</th></tr>
<tr><th>22h</th><th>48h</th><th>22h</th><th>48h</th><th>22h</th><th>48h</th><th>22h</th><th>48h</th><th>22h</th><th>48h</th><th>22h</th><th>48h</th></tr>
<tr><td rowspan="6">Gram Positives</td><td>Bacillus subtilis — NCTC 9372</td><td>>128</td><td>>128</td><td>>32</td><td>>32</td><td>>64</td><td>>64</td><td>>64</td><td>>64</td><td>16</td><td>>64</td><td>64</td><td>>64</td></tr>
<tr><td>Listeria monocytogenes — NCTC 11994</td><td>16</td><td>>128</td><td>16</td><td>16</td><td>>64</td><td>>64</td><td>>64</td><td>>64</td><td>8</td><td>>64</td><td>16</td><td>>64</td></tr>
<tr><td>Staphylococci epidermidis — NCTC 11047</td><td>16</td><td>64</td><td>32</td><td>>32</td><td>16</td><td>32</td><td>16</td><td>16</td><td>16</td><td>>64</td><td>16</td><td>>64</td></tr>
<tr><td>Staphylococcus aureus — NCTC 6571</td><td>16</td><td>64</td><td>32</td><td>>32</td><td>32</td><td>64</td><td>32</td><td>32</td><td>16</td><td>16</td><td>16</td><td>32</td></tr>
<tr><td>Staphylococcus aureus (MRSA) — NCTC 11939</td><td>16</td><td>16</td><td>16</td><td>16</td><td>16</td><td>16</td><td>16</td><td>32</td><td>16</td><td>16</td><td>16</td><td>64</td></tr>
<tr><td>Streptococcus pyogenes — NCTC 8306</td><td>64</td><td>64</td><td>>32</td><td>>32</td><td>>64</td><td>>64</td><td>>64</td><td>>64</td><td>64</td><td>>64</td><td>>64</td><td>>64</td></tr>
</table>

| | 100 | 50 | 25 | 12.5 | 6.25 | 3.1 | 1.5 | 0.75 | 0.38 | 0.2 | 0.1 | NIL |
|---|---|---|---|---|---|---|---|---|---|---|---|---|
| RSV | ++++ | ++++ | ++++ | ++++ | ++++ | ++++ | +--- | ---- | ---- | ---- | ---- | +++ |
| RSV | ++++ | ++++ | ++++ | ++++ | ++++ | ++++ | +--- | ---- | ---- | ---- | ---- | +++ |
| RSV | ++++ | ++++ | ++++ | ++++ | ++++ | +++- | ---- | ---- | ---- | ---- | ---- | +++ |
| RSV | ++++ | ++++ | ++++ | ++++ | ++++ | ++++ | ---- | +--- | ---- | ---- | ---- | +++ |
| RSV | ++++ | ++++ | ++++ | ++++ | ++++ | ++++ | ++-- | ---- | ---- | ---- | ---- | +++ |
| RSV | ++++ | ++++ | ++++ | ++++ | +--- | ---- | ---- | ---- | ---- | ---- | ---- | +++ |
| DMS | ---- | ---- | ---- | +--- | ---- | ---- | ---- | ---- | ---- | ---- | ---- | +++ |
| DMS | ---- | ---- | ---- | ---- | ---- | ---- | ---- | ---- | ---- | ---- | ---- | +++ |

Key

| Sign | Percentage of cells remaining |
|---|---|
| ++++ | 100 |
| +++- | 75 |
| ++-- | 50 |
| +--- | 25 |
| ---- | 0 |

| | 100 | 50 | 25 | 12.5 | 6.25 | 3.1 | 1.5 | 0.75 | 0.38 | 0.2 | 0.1 | NIL |
|---|---|---|---|---|---|---|---|---|---|---|---|---|
| RSV | ++++ | ++++ | ++++ | ++++ | ++++ | ++++ | ---- | ---- | ---- | ---- | ---- | ++++ |
| RSV | ++++ | ++++ | ++++ | ++++ | ++++ | +++- | ---- | ---- | ---- | ---- | ---- | ++++ |
| RSV | ++++ | ++++ | ++++ | ++++ | ++++ | ++++ | ---- | ---- | ---- | ---- | ---- | ++++ |
| RSV | ++++ | ++++ | ++++ | ++++ | +++- | +++- | ---- | ---- | ---- | ---- | ---- | ++++ |
| RSV | ++++ | ++++ | ++++ | ++++ | ++++ | ++++ | ---- | ---- | ---- | ---- | ---- | ++++ |
| DMS | ++++ | ---- | ---- | ---- | ---- | ---- | ---- | ---- | ---- | ---- | ---- | ++++ |
| DMS | ---- | ---- | ---- | ---- | ---- | ---- | ---- | ---- | ---- | ---- | ---- | ++++ |

Key
Sign    Percentage of cells remaining
++++    100
+++-    75
++--    50
+---    25
----    0

ANTIMICROBIAL COMPOUND

CROSS-REFERENCE TO RELATED APPLICATIONS

This application is the U.S. national phase under 35 U.S.C. § 371 of PCT International Application No. PCT/GB2016/051053, which has an international filing date of Apr. 15, 2016 and designated the United States of America, which application claims benefit of priority to GB Application No. 1506448.8, filed Apr. 16, 2015, the disclosures of each of which are incorporated by reference herein.

The present invention relates to antimicrobial compounds for use in treating microbial infections. The invention extends to the compounds per se, pharmaceutical compositions and methods of treating microbial infections.

Over the last forty years, fluorine-containing compounds have played a key role in the development of new pharmaceuticals, crop protection agents and insecticides[2,3] where a significant number of these products contain one or more fluorine atoms[1]. The interest in the use of fluorine as a design component in medicinal chemistry has been largely due to its ability to affect the physicochemical and biological properties of compounds where it is incorporated. The low steric impact of the small van der Waals ratio coupled with its high electronegativity, the ability to participate in hydrogen bonding and the inherent carbon-fluorine bond stability to metabolic transformation are well known features. In addition, there are many examples of the incorporation of the fluorine atom and the range of effect of this substituent, on lipophilicity for example[4]. However, despite this, fluorinated pyridine and pyrimidine nuclei remain relatively understudied and their effects on drug properties relatively undocumented.

There is therefore a need to provide new antimicrobial compounds, which incorporate fluorine. The present invention arose due to the inventor's interest in the development of methodologies to incorporate fluorinated pyridine and pyrimidine nuclei into drug structures with a strong provenance to act as the basis for the development of novel screening collections.

The inventors believe the chemical family they have identified is novel per se.

Hence, in a first aspect of the invention, there is provided a compound of formula (I):

Formula (I)

wherein m is 0, 1, 2, 3, 4 or 5;
n is 0, 1, 2, 3 or 4;
$X^1$ is a $C_{1-5}$ straight or branched alkyl or alkenyl, or a halogen;
$X^2$ is a $C_{1-5}$ straight or branched alkyl or alkenyl, or a halogen;
$Y^1$ is H or a $C_{1-5}$ straight or branched alkyl or alkenyl;
$Y^2$ is H or a $C_{1-5}$ straight or branched alkyl or alkenyl;
$Y^3$ is F, $R^1$, $NR^1R^{1'}$, $OR^1$, $SR^1$, or $SO_2R^1$;
$Y^4$ is F, $R^2$, $NR^2R^{2'}$, $OR^2$, $SR^2$, or $SO_2R^2$;
$Y^5$ is F, $R^3$, $NR^3R^{3'}$, $OR^3$, $SR^3$, or $SO_2R^3$;
Z is N or $CY^6$;
$Y^6$ is F, $R^4$, $NR^4R^{4'}$, $OR^4$, $SR^4$, or $SO_2R^4$; and
$R^1$, $R^{1'}$, $R^2$, $R^{2'}$, $R^3$, $R^{3'}$, $R^4$, and $R^{4'}$ are independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, and $C_{2-4}$ dialkylaminoalkyl, and/or $R^1$ and $R^{1'}$ together with the nitrogen atom to which they are attached, $R^2$ and $R^{2'}$ together with the nitrogen atom to which they are attached, $R^3$ and $R^{3'}$ together with the nitrogen atom to which they are attached, and $R^4$ and $R^{4'}$ together with the nitrogen atom to which they are attached independently form a 3-7 membered ring; wherein at least one of $Y^3$, $Y^4$ and $Y^5$ is F and/or Z is CF;
or a pharmaceutically acceptable salt or solvate thereof.

The inventors have found that compounds of formula (I) may be useful in therapy or as a medicament.

Hence, in a second aspect, there is provided a compound of formula (I):

Formula (I)

wherein m is 0, 1, 2, 3, 4 or 5;
n is 0, 1, 2, 3 or 4;
$X^1$ is a $C_{1-5}$ straight or branched alkyl or alkenyl, or a halogen;
$X^2$ is a $C_{1-5}$ straight or branched alkyl or alkenyl, or a halogen;
$Y^1$ is H or a $C_{1-5}$ straight or branched alkyl or alkenyl;
$Y^2$ is H or a $C_{1-5}$ straight or branched alkyl or alkenyl;
$Y^3$ is F, $R^1$, $NR^1R^{1'}$, $OR^1$, $SR^1$, or $SO_2R^1$;
$Y^4$ is F, $R^2$, $NR^2R^{2'}$, $OR^2$, $SR^2$, or $SO_2R^2$;
$Y^5$ is F, $R^3$, $NR^3R^{3'}$, $OR^3$, $SR^3$, or $SO_2R^3$;
Z is N or $CY^6$;
$Y^6$ is F, $R^4$, $NR^4R^{4'}$, $OR^4$, $SR^4$, or $SO_2R^4$; and
$R^1$, $R^{1'}$, $R^2$, $R^{2'}$, $R^3$, $R^{3'}$, $R^4$, and $R^{4'}$ are independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, and $C_{2-4}$ dialkylaminoalkyl, and/or $R^1$ and $R^{1'}$ together with the nitrogen atom to which they are attached, $R^2$ and $R^{2'}$ together with the nitrogen atom to which they are attached, $R^3$ and $R^{3'}$ together with the nitrogen atom to which they are attached, and $R^4$ and $R^{4'}$ together with the nitrogen atom to which they are attached independently form a 3-7 membered ring;
wherein at least one of $Y^3$, $Y^4$ and $Y^5$ is F and/or Z is CF;
or a pharmaceutically acceptable salt or solvate thereof, for use in therapy.

The inventors have also found that compounds of formula (I) are useful in the treatment of microbial infections.

Hence, in a third aspect, there is provided a compound of formula (I):

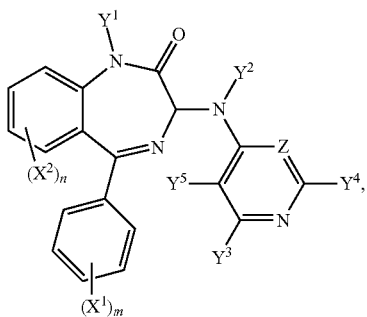

Formula (I)

wherein m is 0, 1, 2, 3, 4 or 5;
n is 0, 1, 2, 3 or 4;
$X^1$ is a $C_{1-5}$ straight or branched alkyl or alkenyl, or a halogen;
$X^2$ is a $C_{1-5}$ straight or branched alkyl or alkenyl, or a halogen;
$Y^1$ is H or a $C_{1-5}$ straight or branched alkyl or alkenyl;
$Y^2$ is H or a $C_{1-5}$ straight or branched alkyl or alkenyl;
$Y^3$ is F, $R^1$, $NR^1R^{1'}$, $OR^1$, $SR^1$, or $SO_2R^1$;
$Y^4$ is F, $R^2$, $NR^2R^{2'}$, $OR^2$, $SR^2$, or $SO_2R^2$;
$Y^5$ is F, $R^3$, $NR^3R^{3'}$, $OR^3$, $SR^3$, or $SO_2R^3$;
Z is N or $CY^6$;
$Y^6$ is F, $R^4$, $NR^4R^{4'}$, $OR^4$, $SR^4$, or $SO_2R^4$; and
$R^1$, $R^{1'}$, $R^2$, $R^{2'}$, $R^3$, $R^{3'}$, $R^4$, and $R^{4'}$ are independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, and $C_{2-4}$ dialkylaminoalkyl, and/or $R^1$ and $R^{1'}$ together with the nitrogen atom to which they are attached, $R^2$ and $R^{2'}$ together with the nitrogen atom to which they are attached, $R^3$ and $R^{3'}$ together with the nitrogen atom to which they are attached, and $R^4$ and $R^{4'}$ together with the nitrogen atom to which they are attached independently form a 3-7 membered ring;
wherein at least one of $Y^3$, $Y^4$ and $Y^5$ is F and/or Z is CF;
or a pharmaceutically acceptable salt or solvate thereof, for use in treating, ameliorating, or preventing a microbial infection.

In a fourth aspect, there is provided a method of treating, ameliorating or preventing a microbial infection, the method comprising administering, to a subject in need of such treatment, a therapeutically effective amount of the compound as previously defined, or a functional analogue, pharmaceutically acceptable salt or solvate thereof.

The microbial infection may comprise a fungal infection.

Alternatively, the microbial infection may comprise a viral infection. Examples of a viral infection which may be treated with compounds of the invention include: Respiratory Syncytial Virus (RSV), Hepatitis C Virus (HCV), Dengue Virus, Ebola virus, Hepatitis B Virus, and Influenza virus.

Alternatively, the microbial infection may comprise a bacterial infection. The bacterial infection may comprise a gram-positive bacterial infection. Examples of gram positive bacterial infection which may be treated with compounds of the invention are preferably selected from a group consisting of: *Staphylococcus* spp.; and *Streptococcus* spp. Preferred species of bacteria, which may be treated, include *S. epidermis*, *S. aureus*, Methicillin-resistant *S. aureus*, and *S. pyogenes*.

Alternatively, the bacterial infection may comprise a gram-negative bacterial infection.

When $R^1$, $R^{1'}$, $R^2$, $R^{2'}$, $R^3$, $R^{3'}$, $R^4$ and/or $R^{4'}$ comprise a $C_{3-6}$ cycloalkyl or cycloalkenyl, the or each $C_{3-6}$ cycloalkyl or cycloalkenyl may independently comprise cyclohexyl or phenyl.

When $R^1$, $R^{1'}$, $R^2$, $R^{2'}$, $R^3$, $R^{3'}$, $R^4$ and/or $R^{4'}$ comprise a $C_{3-6}$ heterocyclyl or heteroaryl, the or each $C_{3-6}$ heterocyclyl or heteroaryl may independently comprise pyridyl, pyrimidyl, furanyl, imidazolyl, piperidinyl, morpholinyl, pyrrolidinyl, thiomorpholinyl or thiomorpholinyl S,S dioxide.

When $R^1$ and $R^{1'}$ together with the nitrogen atom to which they are attached, $R^2$ and $R^{2'}$ together with the nitrogen atom to which they are attached, $R^3$ and $R^{3'}$ together with the nitrogen atom to which they are attached, and/or $R^4$ and $R^{4'}$ together with the nitrogen atom to which they are attached independently form a 3-7 membered ring the or each 3-7 membered ring may comprise a 5 membered ring or a 6 membered ring. The 5 membered ring may comprise pyrrolidine. The 6 membered ring may comprise piperidine, piperazine, morpholine, thiomorpholine or thiomorpholine S,S dioxide. Preferably, the 6 membered ring comprises morpholine.

In one preferred embodiment, Z is N and the compound has a formula (Ia):

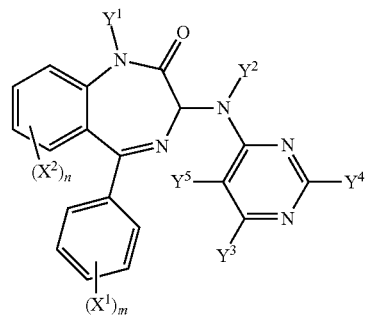

Formula (Ia)

In an alternative preferred embodiment, Z is $CY^6$ and the compound has a formula (Ib):

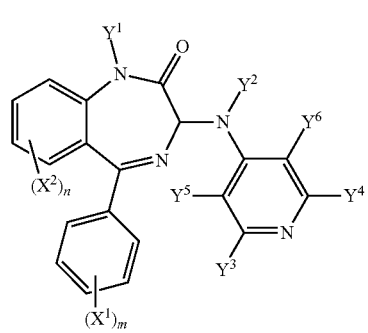

Formula (Ib)

In an even more preferred embodiment $Y^6$ is F and the compound has a formula (Ic)

Formula (Ic)

In a preferred embodiment $Y^3$ is F.
In an alternative preferred embodiment $Y^4$ is F.
In an alternative preferred embodiment $Y^5$ is F.
In a preferred embodiment $Y^4$ is F, $Y^5$ is F, Z is $CY^6$, and $Y^6$ is F.

$Y^3$ may comprise $OR^1$. $R^1$ may comprise a $C_{1-5}$ straight or branched alkyl or alkenyl. $R^1$ may comprise a methyl, ethyl, propyl, butyl or pentyl. Preferably, $R^1$ comprises an ethyl.

$Y^3$ may comprise $SR^1$. $R^1$ may comprise a $C_{1-5}$ straight or branched alkyl or alkenyl. $R^1$ may comprise a methyl, ethyl, propyl, butyl or pentyl. Preferably, $R^1$ comprises a methyl.

$Y^3$ may comprise $SO_2R^1$. $R^1$ may comprise a $C_{1-5}$ straight or branched alkyl or alkenyl. $R^1$ may comprise a methyl, ethyl, propyl, butyl or pentyl. Preferably, $R^1$ comprises a methyl.

$Y^3$ may comprise $NR^1R^{1'}$. $R^1$ and $R^{1'}$ together with the nitrogen atom to which they are attached may independently form a 3-7 membered ring. The 3-7 membered ring preferably comprises morpholinyl.

In an even more preferred embodiment $Y^3$ is F, $Y^4$ is F, $Y^5$ is F, Z is $CY^6$, $Y^6$ is F, and the compound has a formula (Id):

Formula (Id)

In a preferred embodiment n is 0. Accordingly, it will be understood that a hydrogen will be bonded to each of the position 6, 7, 8 and 9 carbons of the benzodiazepine ring structure.

In an alternative embodiment n is 4. Accordingly, an $X^2$ group will be present on each of the position 6, 7, 8 and 9 carbons of the benzodiazepine ring structure.

In an embodiment where n is 1, then an $X^2$ group may be bonded to one of the position 6, 7, 8 and 9 carbons of the benzodiazepine ring structure, and a hydrogen will be bonded to each of the three remaining carbons. In an embodiment where n is 2, then an $X^2$ group may be bonded to two of the position 6, 7, 8 and 9 carbons of the benzodiazepine ring structure, and a hydrogen will be bonded to each of the two remaining carbons. In an embodiment where n is 3, then an $X^2$ group may be bonded to three of the position 6, 7, 8 and 9 carbons of the benzodiazepine ring structure, and a hydrogen will be bonded to the remaining carbon.

In an alternative preferred embodiment n is 1, and the $X^2$ group is bonded to the 7 position carbon and the compound has a formula (Ie):

Formula (Ie)

$X^2$ may be any halogen, such as fluorine, chlorine, bromine or iodine. Preferably, $X^2$ is chlorine. Alternatively, $X^2$ is preferably fluorine. Alternatively, $X^2$ is preferably bromine.

In a preferred embodiment n is 1, and the $X^2$ is a chlorine bonded to the 7 position carbon.

In a preferred embodiment m is 0. Similarly, it will be understood that a hydrogen will be bonded to each of the position 2, 3, 4, 5 and 6 carbons of the phenyl ring structure.

Alternatively, in an embodiment where m is 5, then an $X^1$ group will be present on each of the position 2, 3, 4, 5 and 6 carbons of the phenyl ring structure.

Accordingly, in an embodiment where m is 1, then an $X^1$ group may be bonded to one of the position 2, 3, 4, 5 and 6 carbons of the phenyl ring structure, and a hydrogen will be bonded to each of the four remaining carbons. In an embodiment where m is 2, then an $X^1$ group may be bonded to two of the position 2, 3, 4, 5 and 6 carbons of the phenyl ring structure, and a hydrogen will be bonded to each of the three remaining carbons. In an embodiment where m is 3, then an $X^1$ group may be bonded to three of the position 2, 3, 4, 5 and 6 carbons of the phenyl ring structure, and a hydrogen will be bonded to the two remaining carbons. In an embodiment where m is 4, then an $X^1$ group may be bonded to four of the position 2, 3, 4, 5 and 6 carbons of the phenyl ring structure, and a hydrogen will be bonded to the remaining carbon.

In an alternative preferred embodiment m is 1, and the $X^1$ group is bonded to the 4 position carbon.

$X^1$ may be any halogen, such as fluorine, chlorine, bromine or iodine. Preferably, $X^1$ is chlorine. Alternatively, $X^1$ is preferably fluorine. Alternatively, $X^1$ is preferably bromine.

In a preferred embodiment m is 1, and the $X^1$ is a bromine bonded to the 4 position carbon.

It will be understood that $Y^1$ may comprise a methyl group, an ethyl group, a propyl group, a butyl group or a pentyl group. Similarly, it will be understood that $Y^2$ may comprise a methyl group, an ethyl group, a propyl group, a butyl group or a pentyl group.

In one preferred embodiment, $Y^1$ is a methyl group. In one preferred embodiment $Y^2$ is methyl group.

However, in a more preferred embodiment, $Y^1$ is a hydrogen. In a more preferred embodiment $Y^2$ is hydrogen.

In a further preferred embodiment both $Y^1$ and $Y^2$ are hydrogen and the compound has a formula (If):

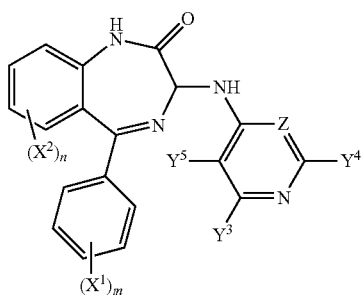

Formula (If)

It will be appreciated that compounds described herein possess a chiral centre at the position 3 carbon of the benzodiazepine ring structure. Accordingly, in one preferred embodiment, the compound may have an S chiral centre and a formula (Ig):

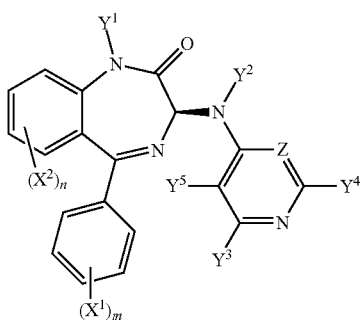

Formula (Ig)

In an alternative preferred embodiment, the compound may have an R chiral centre and a formula (Ih):

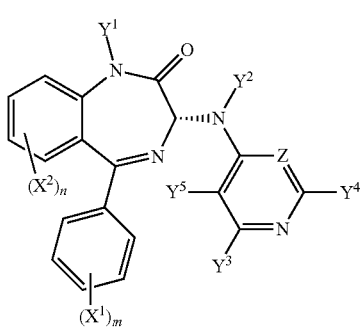

Formula (Ih)

The inventors have shown in the examples that the (S) compound is the more active, and so is preferred.

In a preferred embodiment m is 0; n is 0; $Y^1$ is H; $Y^2$ is H; $Y^3$ is F; $Y^4$ is F; $Y^5$ is F; Z is CF and the compound has a formula (Ij):

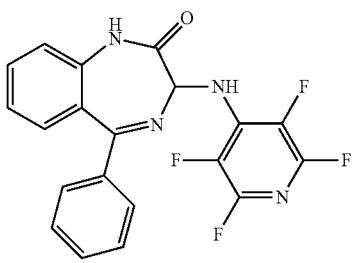

Formula (Ij)

More preferably, the compound of formula (Ij) has an S chiral centre and is a compound of formula (Ik):

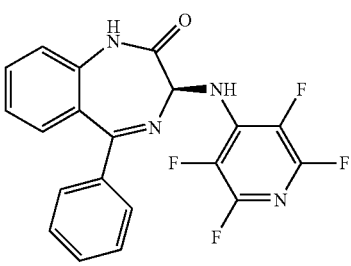

Formula (Ik)

Alternatively, the compound of formula (Ij) has an R chiral centre and is a compound of formula (Il):

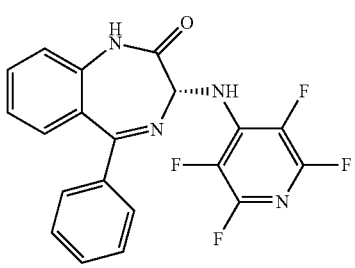

Formula (Il)

In a preferred embodiment m is 0; n is 0; $Y^1$ is H; $Y^2$ is H; $Y^3$ is $OR^1$; $R^1$ is ethyl; $Y^4$ is F; $Y^5$ is F; Z is CF and the compound has a formula (Im):

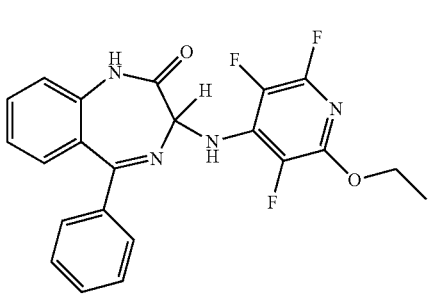

Formula (Im)

It will be appreciated that the compound of formula (Im) is (3)-5-phenyl-3-[(2-ethoxy-3,5,6-trifluoropyridin-4-yl)amino]-2,3-dihydro-1H-1,4-benzodiazepin-2-one.

More preferably, the compound of formula (Im) has an S chiral centre and is (3S)-5-phenyl-3-[(2-ethoxy-3,5,6-trifluoropyridin-4-yl)amino]-2,3-dihydro-1H-1,4-benzodiazepin-2-one.

In a preferred embodiment m is 0; n is 0; P is H; $Y^2$ is H; $Y^3$ is $SR^1$; $R^1$ is methyl; $Y^4$ is F; $Y^5$ is F; Z is CF and the compound has a formula (In):

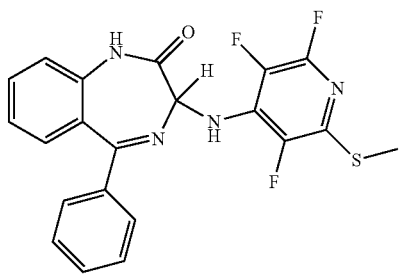

Formula (In)

It will be appreciated that the compound of formula (In) is (3)-5-phenyl-3-[(2,3,6-trifluoro-6-(methylsulphanyl) pyridin-4-yl)amino]-2,3-dihydro-1H-1,4-benzodiazepin-2-one.

More preferably, the compound of formula (In) has an S chiral centre and is (3S)-5-phenyl-3-[(2,3,6-trifluoro-6-(methylsulphanyl) pyridin-4-yl)amino]-2,3-dihydro-1H-1,4-benzodiazepin-2-one.

In a preferred embodiment m is 0; n is 0; P is H; $Y^2$ is H; $Y^3$ is $SO_2R^1$; $R^1$ is methyl; $Y^4$ is F; $Y^5$ is F; Z is CF and the compound has a formula (Io):

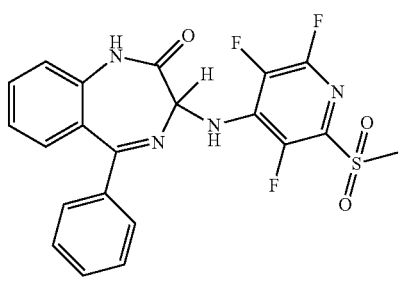

Formula (Io)

It will be appreciated that the compound of formula (Io) is (3)-5-phenyl-3-[(2,3,6-trifluoro-6-methylsulphonyl pyridin-4-yl)amino]-2,3-dihydro-1H-1,4-benzodiazepin-2-one.

More preferably, the compound of formula (Io) has an S chiral centre and is (3S)-5-phenyl-3-[(2,3,6-trifluoro-6-methylsulphonyl pyridin-4-yl)amino]-2,3-dihydro-1H-1,4-benzodiazepin-2-one.

In a preferred embodiment m is 0; n is 0; P is H; $Y^2$ is H; $Y^3$ is $NR^1R^{1'}$; $R^1$ and $R^{1'}$ together with the nitrogen atom to which they are attached independently form a 6 membered ring which comprises morpholinyl; $Y^4$ is F; $Y^5$ is F; Z is CF and the compound has a formula (Ip):

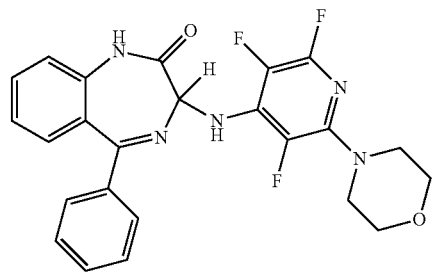

Formula (Ip)

It will be appreciated that the compound of formula (Ip) is (3)-5-phenyl-3-[(2,3,6-trifluoro-6-(morpholin-4-yl) pyridin-4-yl)amino]-2,3-dihydro-1H-1,4-benzodiazepin-2-one.

More preferably, the compound of formula (Ip) has an S chiral centre and is (3S)-5-phenyl-3-[(2,3,6-trifluoro-6-(morpholin-4-yl) pyridin-4-yl)amino]-2,3-dihydro-1H-1,4-benzodiazepin-2-one.

In a preferred embodiment m is 0; n is 1 and $X^2$ is a chlorine bonded to the 7 position carbon; $Y^1$ is H; $Y^2$ is H; $Y^3$ is F; $Y^4$ is F; $Y^5$ is F; Z is CF and the compound has a formula (Iq):

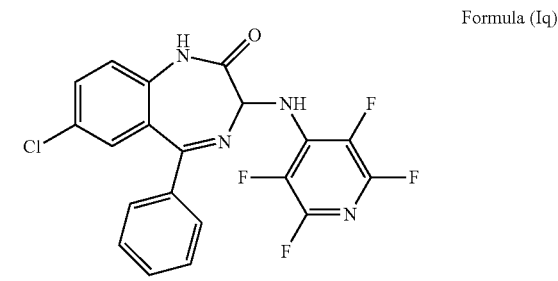 [SMILES: O=C1Nc2ccc(Cl)cc2C(c2ccccc2)=NC1Nc1c(F)c(F)nc(F)c1F]

Formula (Iq)

In a preferred embodiment m is 1 and $X^1$ is a bromine bonded to the 4 position carbon; n is 0; $Y^1$ is H; $Y^2$ is H; $Y^3$ is F; $Y^4$ is F; $Y^5$ is F; Z is CF and the compound has a formula (Ir):

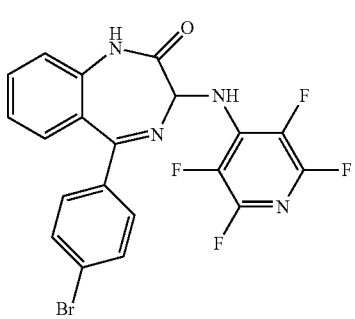

Formula (Ir)

It will be appreciated that the compounds described herein or a pharmaceutically acceptable salt or solvate thereof may be used in a medicament which may be used in a monotherapy (i.e. use of the compound alone), for treating, ameliorating, or preventing a microbial infection. Alternatively, the compounds or a pharmaceutically acceptable salt or solvate thereof may be used as an adjunct to, or in combination with, known therapies for treating, ameliorating, or preventing a microbial infection.

The compounds may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising the compounds described herein may be used in a number of ways. For instance, oral administration may be required, in which case the compound may be contained within a composition that may, for example, be ingested orally in the form of a tablet, capsule or liquid. Compositions comprising the compounds of the invention may be administered by inhalation (e.g. intranasally). Compositions may also be formulated for topical use. For instance, creams or ointments may be applied to the skin.

Compounds according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with compounds used according to the invention is required and which would normally require frequent administration (e.g. at least daily injection).

In a preferred embodiment, compounds and compositions according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the compound that is required is determined by its biological activity and bioavailability, which in turn depends on the mode of administration, the physiochemical properties of the compound, and whether it is being used as a monotherapy, or in a combined therapy. The frequency of administration will also be influenced by the half-life of the compound within the subject being treated. Optimal dosages to be administered may be determined by those skilled in the art, and will vary with the particular compound in use, the strength of the pharmaceutical composition, the mode of administration, and the advancement of the a microbial infection. Additional factors depending on the particular subject being treated will result in a need to adjust dosages, including subject age, weight, gender, diet, and time of administration.

Generally, a daily dose of between 0.01 µg/kg of body weight and 500 mg/kg of body weight of the compound according to the invention may be used for treating, ameliorating, or preventing a microbial infection depending upon which compound or analogue is used. More preferably, the daily dose is between 0.01 mg/kg of body weight and 400 mg/kg of body weight, more preferably between 0.1 mg/kg and 200 mg/kg body weight, and most preferably between approximately 1 mg/kg and 100 mg/kg body weight.

The compound may be administered before, during or after onset of the microbial infection to be treated. Daily doses may be given as a single administration (e.g. a single daily injection). Alternatively, the microbial infection may require administration twice or more times during a day. As an example, compounds according to the invention may be administered as two (or more depending upon the severity of the microbial infection being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of the compounds according to the invention to a patient without the need to administer repeated doses.

Known procedures, such as those conventionally employed by the pharmaceutical industry (e.g. in vivo experimentation, clinical trials, etc.), may be used to form specific formulations comprising the compounds according to the invention and precise therapeutic regimes (such as daily doses of the compounds and the frequency of administration). The inventors believe that they are the first to describe a pharmaceutical composition for treating a microbial infection, based on the use of the compounds of the invention.

Hence, in a fifth aspect of the invention, there is provided a pharmaceutical composition comprising a compound according to the first aspect, or a pharmaceutically acceptable salt or solvate thereof, and a pharmaceutically acceptable vehicle.

The pharmaceutical composition can be used in the therapeutic amelioration, prevention or treatment in a subject of a microbial infection. Thus, the composition is preferably an antimicrobial pharmaceutical composition.

The invention also provides, in a sixth aspect, a process for making the composition according to the fifth aspect, the process comprising contacting a therapeutically effective amount of a compound of the first aspect, or a pharmaceutically acceptable salt or solvate thereof, and a pharmaceutically acceptable vehicle.

Preferably, the compound has any of the formulae shown as formula I, Ia-Ir.

A "subject" may be a vertebrate, mammal, or domestic animal. Hence, compounds, compositions and medicaments according to the invention may be used to treat any mammal, for example livestock (e.g. a horse), pets, or may be used in other veterinary applications. Most preferably, however, the subject is a human being.

A "therapeutically effective amount" of compound is any amount which, when administered to a subject, is the amount of drug that is needed to treat the target disease, or produce the desired effect, i.e. inhibit microbial infections.

For example, the therapeutically effective amount of compound used may be from about 0.01 mg to about 800 mg, and preferably from about 0.01 mg to about 500 mg. It is preferred that the amount of compound is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents (i.e. the compound according to the first, second and third aspects) according to the invention. In tablets, the active compound may be mixed with a vehicle having the necessary compression properties in suitable proportions and compacted in the shape and size desired. The powders and tablets preferably contain up to 99% of the active compound. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The compound according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The compound may be prepared as a sterile solid composition that may be dissolved or suspended at the time of administration using sterile water, saline, or other appropriate sterile injectable medium.

The compound and compositions of the invention may be administered in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compounds used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The inventors believe that their method of manufacturing the compound of the first aspect is also novel.

Hence, in accordance with a seventh aspect, there is provided a method of manufacturing the compound of the first aspect, the method comprising contacting an amide with a fluorinated heteroaromatic compound selected from the group consisting of a fluorinated pyridine and a fluorinated 1,3-diazine, characterised in that the method uses a ratio of less than 3:1 amide:fluorinated heteroaromatic compound.

Preferably, the ratio of amide:fluorinated heteroaromatic compound is less than 2:1, and is more preferably about 1:1. Ratios of 1:2 and 1:3 amide:fluorinated heteroaromatic compound may also be used.

Preferably, the amide is 3-amino-5-phenyl-2,3-dihydro-1H-1,4-benzodiazepin-2-one. The amide may be racemic 3-amino-5-phenyl-2,3-dihydro-1H-1,4-benzodiazepin-2-one. Alternatively, the amide may be R-3-amino-5-phenyl-2,3-dihydro-1H-1,4-benzodiazepin-2-one or S-3-amino-5-phenyl-2,3-dihydro-1H-1,4-benzodiazepin-2-one.

Preferably, the fluorinated heteroaromatic compound comprises a fluorinated pyridine. Preferably, the fluorinated pyridine comprises pentafluoropyridine.

Alternatively, the fluorinated heteroaromatic compound may comprise a fluorinated 1,3-diazine. Preferably, the fluorinated 1,3-diazine comprises tetrafluoro-1,3-diazine.

The reaction may be carried out in a solution comprising dimethyl formamide (DMF), tetrahydrofuran (THF) and/or acetonitrile. Preferably, the reaction is carried out in a solution comprising dimethyl formamide.

Preferably, the solution is stirred for at least 1 hour. More preferably, the solution is stirred for at least 2, 3, 4 or 5 hours. Most preferably, the solution is stirred for at least 10 or 15 hours.

Preferably, the method comprises extracting an N-substituted fluoropyridine or N-substituted fluorinated 1,3-diazine from the solution. Preferably, the method comprises extracting the N-substituted tetrafluoropyridine from the solution.

The method may comprise subsequently contacting the N-substituted fluoropyridine or N-substituted fluorinated 1,3-diazine with a nucleophile. The nucleophile may comprise an alcohol, a thiol, a thiolate or an amine. The alcohol may comprise methanol, ethanol, propanol, butanol or pentanol. The thiol may comprise methanethiol, ethanethiol, propanethiol, butanthiol or pentanthiol. The thiolate may comprise methanethiolate, ethanethiolate, propanethiolate, butanthiolate or pentanthiolate. The amine may comprise pyrrolidine, piperidine, piperazine, morpholine, thiomorpholine or or thiomorpholine S,S dioxide.

In a further aspect, there is provided a compound of formula (I):

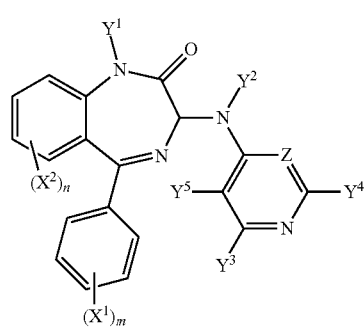

Formula (I)

wherein m is 0, 1, 2, 3, 4 or 5;

n is 0, 1, 2, 3 or 4;

$X^1$ is a $C_{1-5}$ straight or branched alkyl or alkenyl, or a halogen;

$X^2$ is a $C_{1-5}$ straight or branched alkyl or alkenyl, or a halogen;

$Y^1$ is H or a $C_{1-5}$ straight or branched alkyl or alkenyl;

Y² is H or a C₁₋₅ straight or branched alkyl or alkenyl;
Y³ is F, R¹, NR¹, OR¹, or SO₂R¹;
Y⁴ is F, R², NR², OR², or SO₂R²;
Y⁵ is F, R³, NR³, OR³, or SO₂R³;
Z is N or CY⁶;
Y⁶ is F, R⁴, NR⁴, OR⁴, or SO₂R⁴; and
R¹, R², R³ and R⁴ are independently selected from the group consisting of: hydrogen, a $C_{1-5}$ straight or branched alkyl or alkenyl, $C_{3-6}$ cycloalkyl or cycloalkenyl, $C_{3-6}$ heterocyclyl or heteroaryl, $C_{2-4}$ methane sulphonyl alkyl, and $C_{2-4}$ dialkylaminoalkyl; wherein at least one of Y³, Y⁴ and Y⁵ is F and/or Z is CF;

or a pharmaceutically acceptable salt or solvate thereof.

The compound of the further aspect may be for use in therapy. More preferably, the compound of the further aspect may be for use in treating, ameliorating, or preventing a microbial infection.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 6b shows the crystal structure of the molecule (11) of FIG. 6a;

FIG. 7b shows the crystal structure of the molecule (12) of FIG. 7a;

FIG. 10 is a table showing the antimicrobial activity of the synthesised compounds;

FIG. 13 is a table showing the antimicrobial activity of the isolated R and S enantiomers of compound (5);

Figure 1:
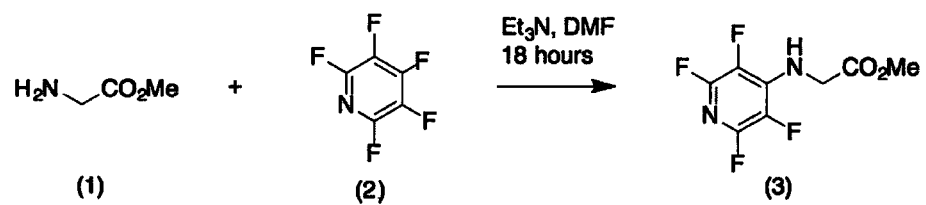
FIG. 1 shows the reaction of glycine methyl ester (1) and pentafluoropyridine (2)

EXAMPLE 1: SYNTHESIS OF COMPOUNDS CONTAINING FLUORINATED PYRIDINE AND PYRIMIDINE GROUPS

The inventors' design principle was based upon the contribution of fluorinated pyridine and pyrimidine groups to physicochemical and biological properties of drug templates whilst maintaining overall steric features and the potential for biological efficacy. As part of this concept of incorporating known drug fragments bound to these fluoroheterocycles, the inventors looked at a range of drug template amines including the benzodiazepine amine (4), shown as the starting material in the reaction of FIG. 2.

Experimental

Melting points were determined in open capillaries, using a Stuart SMP30 digital melting point apparatus and are uncorrected. NMR spectra were recorded on a Bruker Avance-III-400 (1H=400.06 MHz; 19F=376.4 MHz; 13C=100.6 MHz) at ambient probe temperature (nominal 295K) using either deuterated chloroform (CDCl₃) or hexadeuterated dimethylsulphoxide (DMSO-d6) as solvents. Chemical shifts (δ) are given in ppm vs. TMS (¹H NMR, ¹³C NMR) as an internal reference. Coupling constants are given in Hertz (Hz). LC ES MS (positive ion) was performed on a QToF Premier mass spectrometer equipped with an Acquity UPLC (Waters Corp.). The LC separation was achieved on a C18 BEH chromatography column (2.1 mm×100 mm and 1.7 um particle size) using a reverse phase gradient of 100% aqueous (0.1% formic acid in water) to 100% organic (0.1% formic acid in acetonitrile) at 0.6 mL/min. Silica gel plates, Supelco. S-A (Fluorescence Indicator at 254 nM) (Sigma-Aldrich Chemie GmbH Riedstr. 2D-8955T, Steinheim 497329-970, Germany) were used for TLC testing. Column chromatography was performed using silica gel (70-230 mesh) from Sigma-Aldrich (The Old Brickyard, Gillingham, SP8 4JL. UK). Reagents were also obtained from Sigma-Aldrich and used without further purification. Benzodiazepines (4) and (7) were prepared according to the literature procedures[5,10,16].

General Procedure for the Synthesis of N-Substituted Tetrafluoropyridines (3, 6, 11 and 12)

Pentafluoropyridine (1.5 mmoles, 0.144 ml) was added to a solution of the amide (0.5 mmoles) and triethylamine (1.0 mmoles, 0.128 ml) in dimethyl formamide (2 ml) in a 5 ml sample vial and the vial sealed. The resulting solution was stirred overnight (18 hours). The mixture was partitioned between ethyl acetate and water (25 ml volume of each) before successive washing of the ethyl acetate layer with water (×5), brine and dried over sodium sulphate. Chromatography on silica (200/8/1 dichloromethane/ethanol/ammonia) provided isolation of the desired tetrafluoropyridine.

Methyl 2-[(tetrafluoropyridin-4-yl)amino]acetate (3)[7]

Yield: 0.221 g (87%); white solid; mp 67.8-68.7° C. (Lit. 67-69° C.[7]). ¹H NMR (400 MHz, CDCl₃): δ=5.22 (bs, 1H, NH), 4.32 (dt, 2H, J=5.3 Hz, 2.1 Hz, CH₂), 3.85 (s, 3H, OCH₃). ¹³C NMR (100 MHz, CDCl₃): δ=170.03, 145.27, 145.33, 142.91, 142.83, 136.80, 132.80, 130.28, 52.82, 45.48. $^{19}$F (376 MHz, CDCl$_3$) −93.61 (m, 2F, 2 and 6 F), −163.97 (m, 2F, 3 and 5 F): Elemental analysis calcd. for C$_8$H$_6$F$_4$N$_2$O$_2$: C, 40.35; H, 2.54; N, 11.76. Found: C, 40.16; H, 2.56; N, 11.75.

Phenyl-1-(tetrafluoropyridin-4-yl)-3-[(tetrafluoropyridin-4-yl)amino]-2,3-dihydro-1H-1,4-benzodiazepin-2-one (6)

Yield: 0.232 g (84%); white solid; mp 215.2-215.9° C. $^1$H NMR (400 MHz, CDCl$_3$): δ=7.67-7.54 (m, 5H, ArH), 7.50-7.54 (m, 3H, ArH), 7.12 (d, 1H, J=7.12 Hz, ArH), 6.525 (d, 1H, dt, J=6.52 Hz, CHNH), 5.765 (dt, 1H, J=5.77 Hz, 1 Hz, CHNH): $^{13}$C NMR (100 MHz, CDCl$_3$): δ=168.52, 165.13, 145.33, 145.09, 142.97, 142.83, 138.63, 137.40, 135.55, 133.05, 132.91, 131.60, 131.03, 130.45, 130.12, 129.51, 128.70, 127.23, 123.00, 70.56. $^{19}$F (376 MHz, CDCl$_3$) −86.98 (m, 2F, 2' and 6' F), −93.08 (m, 2F, 2 and 6 F), −140.74 (m, 1F, 5'F), −146.15 (m, 1F, 3'F), −161.83 (m, 2F, 3 and 5 F): MS (EI) m/z: 550.09 [M+1]+; HRMS (ESI-TOF) m/z: [M+H]+ Calcd for C$_{25}$H$_{12}$N$_5$OF$_8$ 550.0914; Found 550.0924. Elemental analysis calcd. for C$_{25}$H$_{12}$F$_8$N$_5$O. 0.5H$_2$O: C, 53.77; H, 2.17; N, 12.54. Found: C, 53.80; H, 2.04; N, 12.41.

1,3-bis(tetrafluoropyridin-4-yl)-2,3-dihydro-1H-1,3-benzodiazol-2-one (11)

Yield: 0.138 g (64%); white solid; mp 154.9-156° C. $^1$H NMR (400 MHz, CDCl$_3$): δ=7.34 (m, 2H, ArH), 7.31 (m, 2H, ArH). $^{13}$C NMR (100 MHz, CDCl$_3$): δ=147.70, 145.26, 142.82, 139.82, 137.44, 127.66, 124.56, 110.09: $^{19}$F (376 MHz, CDCl$_3$) −86.34 (m, 2F, 2 and 6 F), −141.42 (m, 2F, 3 and 5 F): MS (EI) m/z: 433.03 [M+1]+; HRMS (ESI-TOF) m/z: [M+H]+ Calcd for C$_{17}$H$_5$F$_8$N$_4$O, 433.0336; Found 433.0320. Elemental analysis calcd. for C$^{17}$H$^5$F$^8$N$^4$O: C, 47.24; H, 0.93; N, 12.96. Found: C, 47.65; H, 1.27; N, 12.60.

1-(tetrafluoropyridin-4-yl)-2,3-dihydro-1H-indole-2,3-dione (12)

Yield: 0.078 g (52%); orange solid; mp 160.3-162.6° C. $^1$H NMR (400 MHz, CDCl$_3$): δ=7.84 (m, 1H, ArH), 7.73 (m, 1H, ArH), 7.36 (m, 1H, ArH), 6.82 (m, 1H, ArH). $^{13}$C NMR (100 MHz, CDCl$_3$): δ=179.23, 155.29, 147.78, 145.27, 142.83, 139.64, 138.99, 137.00, 126.47, 125.82, 124.07, 118.19, 111.48: $^{19}$F (376 MHz, CDCl$_3$) −86.22 (m, 2F, 2 and 6 F), −140.57 (m, 2F, 3 and 5 F): MS (EI) m/z: 401.10 [M+1]+; HRMS (ESI-TOF) m/z: [M+H]+ Calcd for C$_{13}$H$_5$F$_4$N$_2$O$_2$ 297.0287; Found 297.0289. Elemental analysis calcd. for C$_{13}$H$_5$F$_4$N$_2$O$_2$: C, 52.72; H, 1.36; N, 9.46. Found: C, 52.43; H, 1.39; N, 9.45.

Procedure for the synthesis of 5-Phenyl-3-[(tetrafluoropyridin-4-yl)amino]-2,3-dihydro-1H-1,4-benzodiazepin-2-one (5)

Pentafluoropyridine (0.5 mmoles, 0.048 ml) was added to a solution of racemic 3-amino-5-phenyl-2,3-dihydro-1H-1,4-benzodiazepin-2-one (4) (0.5 mmoles, 126 mg) and triethylamine (1.0 mmoles, 0.128 ml) in dimethyl formamide (2 ml) in a 5 ml sample vial and the vial sealed. The resulting solution was stirred overnight (18 hours). The mixture was partitioned between ethyl acetate and water (25 ml volume of each) before successive washing of the ethyl acetate layer with water (×5), brine and dried over sodium sulphate. Chromatography on silica (200/8/1 dichloromethane/ethanol/ammonia) provided isolation of the desired tetrafluoropyridine.

Yield: 0.107 g (54%); white solid; mp 221.5-222.4° C. $^1$H NMR (400 MHz, CDCl$_3$): δ=9.64 (s, 1H, CONH), 7.71 (m, 1H, ArH), 7.54-7.32 (m, 5H, ArH), 7.32 (m, 2H, ArH), 6.74 (d, 1H, J=5.6 Hz, CHNH), 5.44 (d, 1H, J=5.43 Hz, CHNH). $^{13}$C NMR (100 MHz, CDCl$_3$): δ=168.33, 168.22, 145.39, 143.02, 138.31, 136.97, 135.91, 133.00, 132.71, 131.43, 131.04, 130.47, 129.80, 128.43, 127.51, 124.72, 121.67: $^{19}$F (376 MHz, CDCl$_3$) −93.60 (m, 2F, 2 and 6 F), −161.86 (m, 2F, 3 and 5 F): MS (EI) m/z: 401.10 [M+1]+; HRMS (ESI-TOF) m/z: [M+H]+ Calcd for C$_{20}$H$_{13}$F$_4$N$_4$O, 401.1025; Found 401.1021. Elemental analysis calcd. for C$_{20}$H$_{13}$F$_4$N$_4$O. 0.5H2O: C, 58.68; H, 3.20; N, 13.69. Found: C, 58.55; H, 3.01; N, 13.94.

Procedure for the synthesis of 5-Phenyl-1-[(tetrafluoropyridin-4-yl)amino]-2,3-dihydro-1H-1,4-(3-chlorbenzo)-diazepin-2-one

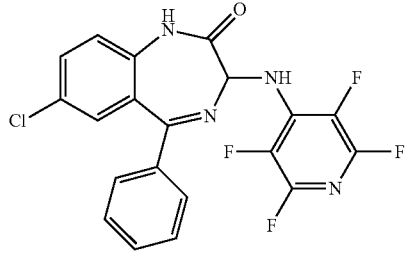 [SMILES: O=C1Nc2ccc(Cl)cc2C(c2ccccc2)=NC1Nc1c(F)c(F)nc(F)c1F]

3-amino-5-phenyl-2,3-dihydro-1H-1,4-(3-chlorobenzo)-diazepin-2-one was prepared from 2-amino-5-chlorobenzophenone according to known procedures.

Pentafluoropyridine (0.5 mmoles, 0.048 ml) was added to a solution of 3-amino-5-phenyl-2,3-dihydro-1H-1,4-(3-chlorobenzo)-diazepin-2-one (0.5 mmoles, 126 mg) and triethylamine (1.0 mmoles, 0.128 ml) in dimethyl formamide (2 ml) in a 5 ml sample vial and the vial sealed. The resulting solution was stirred overnight (18 hours). The mixture was partitioned between ethyl acetate and water (25 ml volume of each) before successive washing of the ethyl acetate layer with water (×5), brine and dried over sodium sulphate. Chromatography on silica (200/8/1 dichloromethane/ethanol/ammonia) provided isolation of 5-Phenyl-3-[(tetrafluoropyridin-4-yl)amino]-2,3-dihydro-1H-1,4-(3-chlorbenzo)-diazepin-2-one.

Procedure for the synthesis of 5-(4-Bromphenyl)-3-[(tetrafluoropyridin-4-yl)amino]-2,3-dihydro-1H-1,4-benzodiazepin-2-one

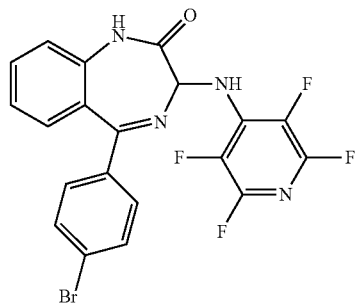 [SMILES: O=C1Nc2ccccc2C(c2ccc(Br)cc2)=NC1Nc1c(F)c(F)nc(F)c1F]

3-amino-5-(4-bromophenyl)-2,3-dihydro-1H-1,4-benzodiazepin-2-one was prepared from 2-amino-4'-bromobenzophenone according to known procedures.

Pentafluoropyridine (0.5 mmoles, 0.048 ml) was added to a solution of 3-amino-5-(4-bromophenyl)-2,3-dihydro-1H-1,4-benzodiazepin-2-one (0.5 mmoles, 126 mg) and triethylamine (1.0 mmoles, 0.128 ml) in dimethyl formamide (2 ml) in a 5 ml sample vial and the vial sealed. The resulting solution was stirred overnight (18 hours). The mixture was partitioned between ethyl acetate and water (25 ml volume of each) before successive washing of the ethyl acetate layer with water (×5), brine and dried over sodium sulphate. Chromatography on silica (200/8/1 dichloromethane/ethanol/ammonia) provided isolation of 5-(4-Bromphenyl)-3-[(tetrafluoropyridin-4-yl)amino]-2,3-dihydro-1H-1,4-benzodiazepin-2-one.

Single-Crystal X-Ray Crystallography

Crystals suitable for single-crystal X-ray diffraction were selected, coated in perfluoropolyether oil, and mounted on MiTeGen sample holders. Diffraction data were collected on a Bruker D8 Venture three-circle diffractometer utilizing mirror-monochromated Mo K α radiation ($\lambda$=0.71073 Å) from an I μS microfocus sealed X-ray tube (Incoatec, Germany) operated at 50 kV and 1 mA, equipped with a PHOTON area detector. The instrument was attached with an open-flow N2 Cryostream device and measurements were performed at 120 K. For data reduction, the Bruker ApeX2 software suite (Bruker AXS) was used. Subsequently, the structures were solved using the Olex2.solve charge-flipping algorithm, and were subsequently refined with Olex2.refine using Gauss-Newton minimization as implemented in Olex2[17]. All non-hydrogen atom positions were located from the Fourier maps and refined anisotropically. Hydrogen atom positions were calculated using a riding model in geometric positions and refined isotropically.

Crystal structure of phenyl-1-(tetrafluoropyridin-4-yl)-3-[(tetrafluoropyridin-4-yl)amino]-2,3-dihydro-1H-1,4-benzodiazepin-2-one (6)

$C_{26}H_{12}F_8N_4O$, $M_r$=549.39, monoclinic, $P2_1/c$, a=11.0830(12) Å, b=15.0739(16) Å, c=13.7407(14) Å, $\beta$=103.273(3)°, $\alpha$=$\gamma$=90°, V=2234.3(4) Å$^3$, T=120 K, Z=4, Z'=1, μ (Mo K$_a$)=0.150, 52791 reflections measured, 4389 unique ($R_{int}$=0.1874) which were used in all calculations. The final wR$_2$ was 0.1048 (all data) and R$_1$ was 0.0511 (I≥2σ(I)).

Crystal structure of 5-Phenyl-3-[(tetrafluoropyridin-4-yl)amino]-2,3-dihydro-1H-1,4-benzodiazepin-2-one (5)

$C_{20}H_{12}F_4N_4O$, $M_r$=400.34, triclinic, P-1, a=7.7420(6) Å, b=8.9135(6) Å, c=13.2209(10) Å, $\alpha$=87.788(2)°, $\beta$=76.248(2)°, Y=75.329(2)°, V=857.08(11) Å$^3$, T=120 K, Z=2, Z'=1.000, μ (Mo K$_a$)=0.129, 20725 reflections measured, 3362 unique ($R_{int}$=0.0783) which were used in all calculations. The final wR$_2$ was 0.1567 (all data) and R$_1$ was 0.0540 (I≥2σ(I)).

Crystal structure of 1,3-bis(tetrafluoropyridin-4-yl)-2,3-dihydro-1H-1,3-benzodiazol-2-one (11)

$C_{17}H_4N_4OF_8$, $M_r$=432.23, monoclinic, $P2_1/c$, a=8.8921(6) Å, b=17.0807(11) Å, c=10.7761(6) Å, $\beta$=104.696(2)°, $\alpha$=$\gamma$=90°, V=1583.17(17) Å$^3$, T=120 K, Z=4, Z'=1, μ (Mo K$_a$)=0.182, 35764 reflections measured, 3108 unique ($R_{int}$=0.0895) which were used in all calculations. The final wR$_2$ was 0.1325 (all data) and R$_1$ was 0.0470 (I≥2σ(I)).

Crystal structure of 1-(tetrafluoropyridin-4-yl)-2,3-dihydro-1H-indole-2,3-dione (12)

$C_{13}H_4F_4N_2O_2$, $M_r$=296.18, monoclinic $P2_1/n$, a=11.137(1) Å, b=8.7314(9) Å, c=11.832(1) Å, $\beta$=98.495(3)°, V=1138.0(2) Å$^3$, Z=4, T=120 K, μ (Mo K$_a$)=0.162 mm$^{-1}$, 21212 reflections measured, 2235 unique ($R_{int}$=0.0695) which were used in all calculations. The final wR$_2$ was 0.1813 (all data) and R$_1$ was 0.0730 (I≥2σ(I)).

Results and Discussion

The reactions of pentafluoro-pyridines are well documented[6] and the inventors decided to use this knowledge to target structures containing nitrogen and oxygen nucleophiles where reactions were both selective and high yielding. An example of the reaction is shown for the reaction of glycine methyl ester (1) with pentafluoro-pyridine (F$_5$Pyr) (2), as shown in FIG. 1.

The amino acid (i) and F$_5$Pyr (2) were reacted according to the experimental procedure defined above. In order to minimise the effect of the volatility of F$_5$Pyr (2), a three-fold excess of this reagent was employed. This procedure employed a reaction time of 18 hours and subsequent work up employed multiple aqueous washings to remove the solvent. The procedure worked well (yield 82%), a significant improvement in yield over that reported previously both in terms of yield and conditions. Structure could be confirmed by both 1H NMR and $^{19}$F NMR analysis of the product (3). This showed signals for the 2,6 and 3,5 position fluorine atoms at -93.6 ppm and -163.98 ppm by comparison with those published for this compound at -93.8 and -166.7 ppm[7].

With the clear success of this approach, the inventors applied this methodology to the benzodiazepine amine (4). This amine (4) was selected as an example of a chemical template of good drug provenance.

Figure 2:
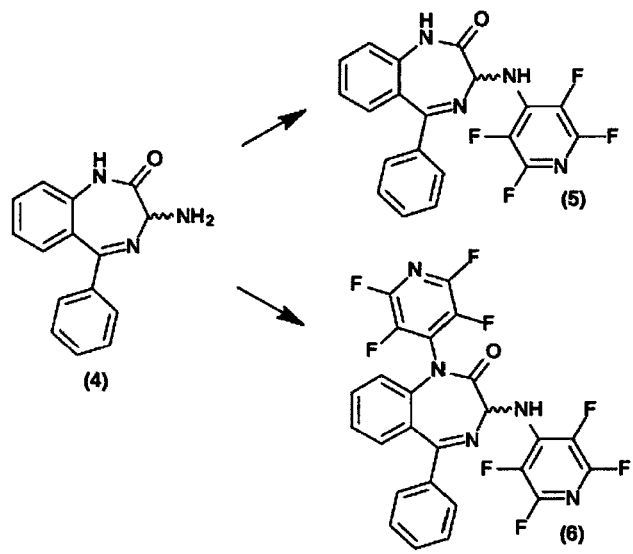
FIG. 2 shows the potential products of the reaction of 1,4-benzodiazepine (4) with pentafluoropyridine.

It was expected that the reaction of the benzodiazepine amine (4) using the conditions described above would provide the mono-tetrafluoropyridyl product (5), shown in FIG. 2. However, the benzodiazepine amine surprisingly reacted in a non-selective fashion and the bis-tetrafluoropyridine derivative (6), also shown in FIG. 2, was isolated as the sole product. Under these conditions the reaction produced the bis-tetrafluoropyridine derivative (6) as the sole product in 84% yield.

Figure 3A:
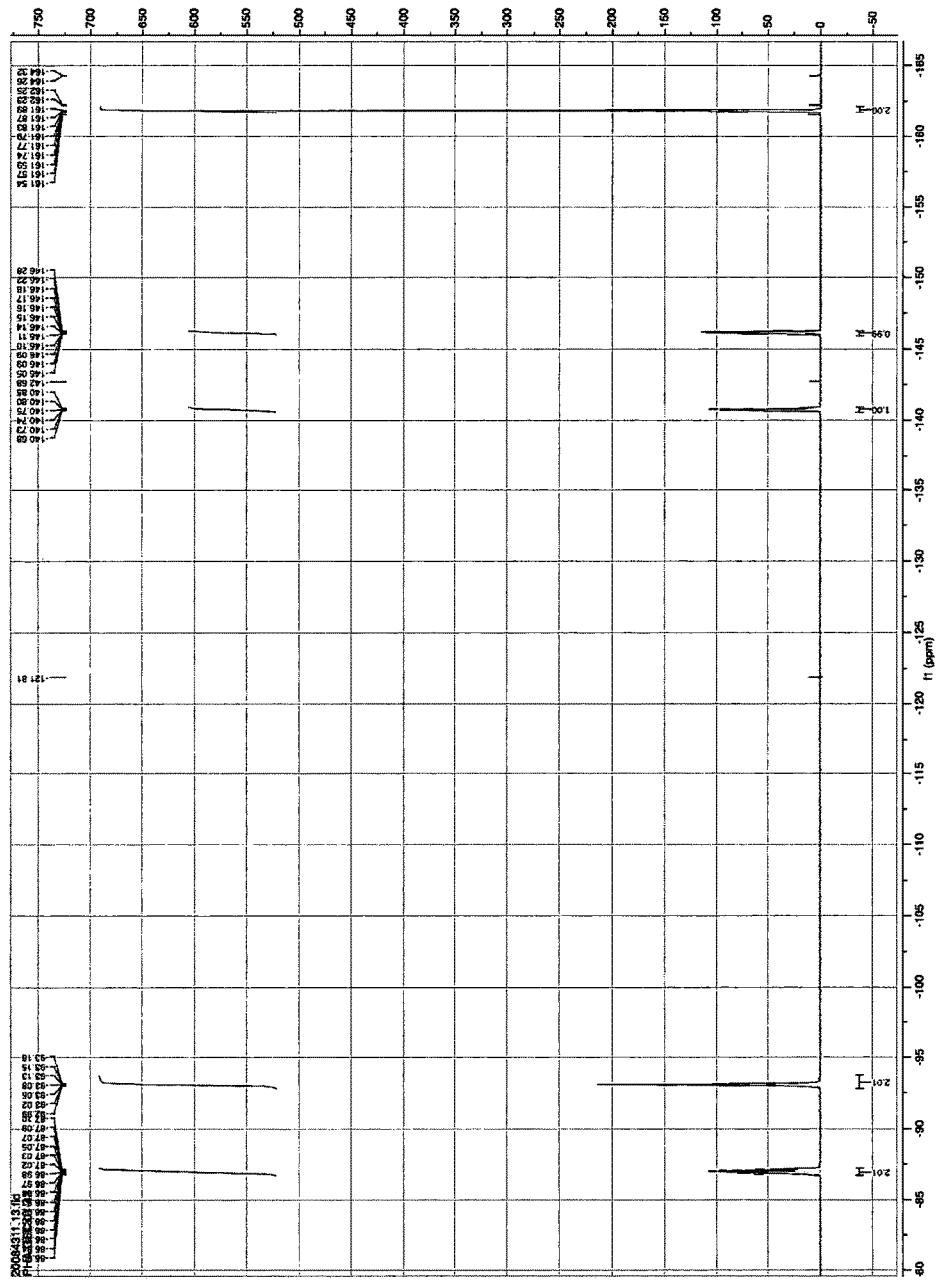
FIG. 3a is a ¹⁹F NMR spectrum of bis tetrafluoropyridine benzodiazepine (6), one of the products shown in FIG. 2.
Figure 3B:
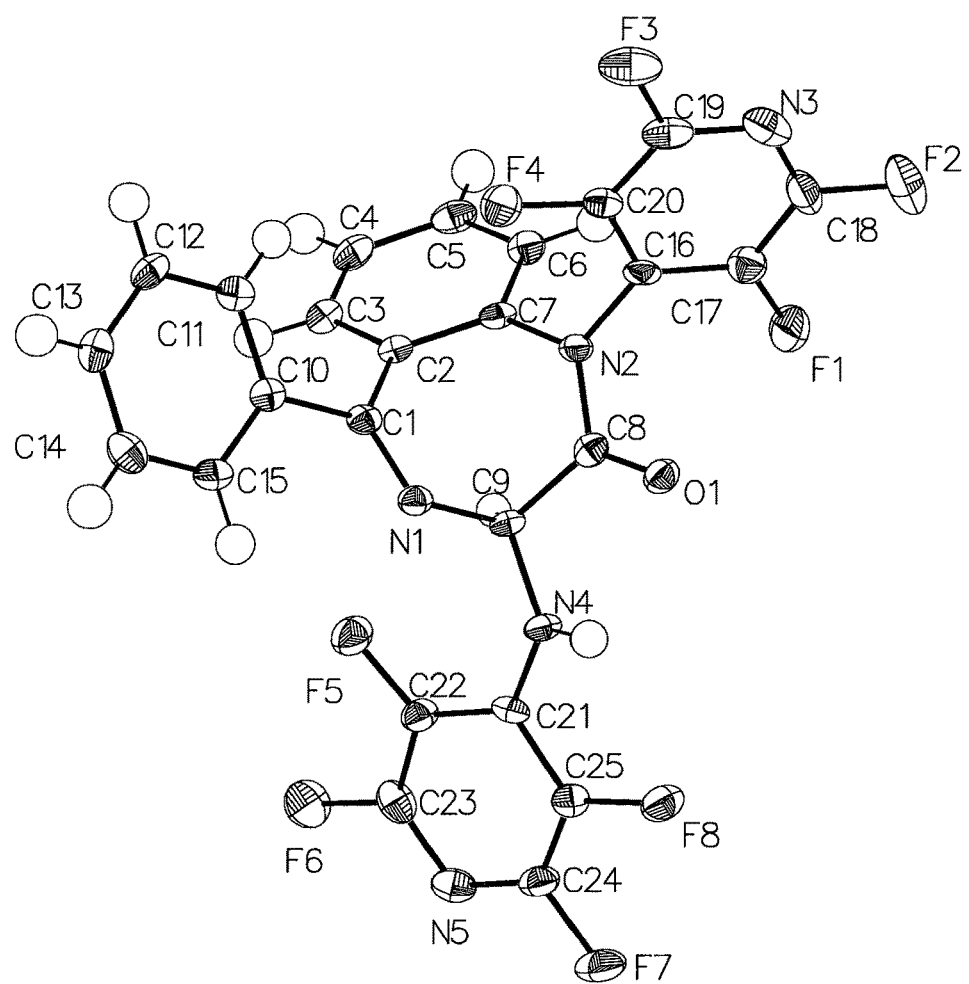
FIG. 3b shows an x-ray structure of bis tetrafluoropyridine substituted benzodiazepine (6), one of the products shown in FIG. 2.

Initial spectroscopic characterisation of the bis-tetrafluoropyridine derivative (6) was provided by NMR. The loss of the benzodiazepine amide (4) NH signal in the $^1$H NMR was apparent and doubling of the pyridine carbon signals were observed in the $^{13}$C. In addition a specific pattern was observed in the $^{19}$F NMR, see FIG. 3a. This pattern was strongly suggestive of a system containing two tetrafluoropyridine rings. Signals that integrated as two fluorines were observed at -93.08 and -161.83 ppm. These were close in shift to those reported previously for analogues of mono-substituted tetrafluoropyridine (3), such as the product obtained from the reaction shown in FIG. 1, and could be assigned to the fluorines at the two and three position of the pyridine ring respectively. Additionally, signals were observed at -87.03 ppm, corresponding to two fluorines and single fluorine signals at -140.74 and -146.44 ppm. A tetrafluoropyridine ring system experiencing an unsymmetrical environment was a logical proposal for this second ring. A confirmation of this analysis was provided by an X-ray structure of the bis-tetrafluoropyridine derivative (6), see FIG. 3b. In this structure, two tetrafluoropyridine rings were observed, substituting both the primary amine functionality and the diazepine ring amide nitrogen.

The reaction of the penta-fluoropyridine with the diazepine ring amide nitrogen is surprising under these conditions. The literature to this point describes no examples of amides reacting under these mild conditions. Usually, more forcing conditions are required, utilizing raised temperature and the formation of nucleophillic amide or imide anionic species in order to facilitate reaction[6,8,9].

The surprising formation of this bis-tetrafluoropyridine adduct ($F_4Pyr)_2BZD$ (6) was further investigated.

Figure 4:
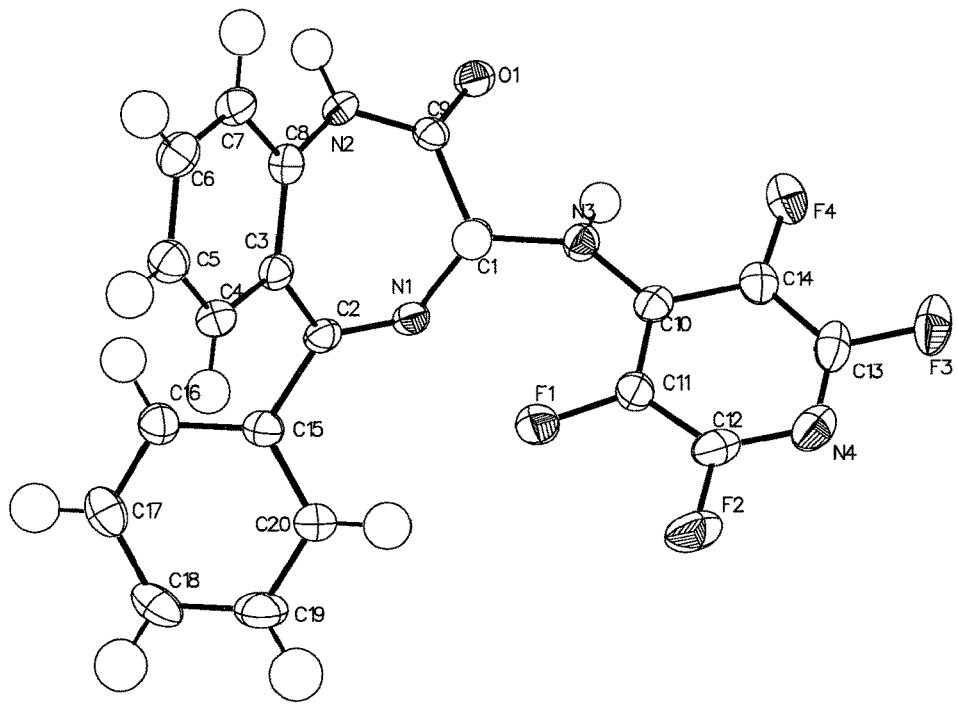
FIG. 4 shows the x-ray structures of the mono-tetrafluorpyrinylated adduct (5), which is a product of the reaction shown in FIG. 2.

Firstly, the benzodiazepine amine (4) was subjected to the same conditions as those utilized previously except only one equivalent of pentafluoropyridine was used. Under these conditions, as expected, only the mono-tetrafluoropyridyl product (5) was observed, the more nucleophillic amine centre reacting with the electrophile preferentially as expected. The crystal structure of the mono-tetrafluoropyridyl product (5) is shown in FIG. 4.

Figure 5:
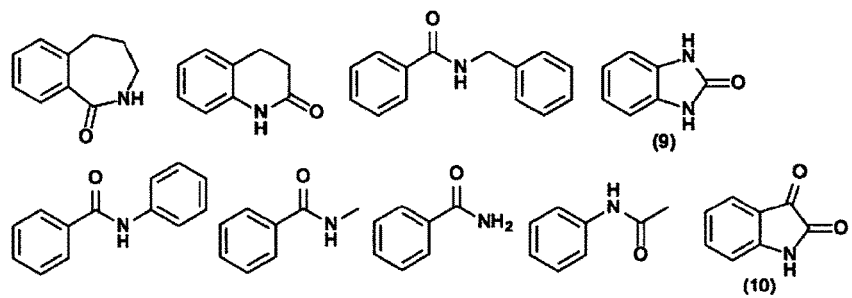
FIG. 5 shows amides which were subjected to standard reaction conditions.
Figure 6A:
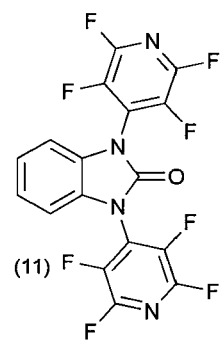
FIG. 6a shows the product (11) of the reaction of cyclic urea (9) and pentafluoropyridine.
Figure 6B:
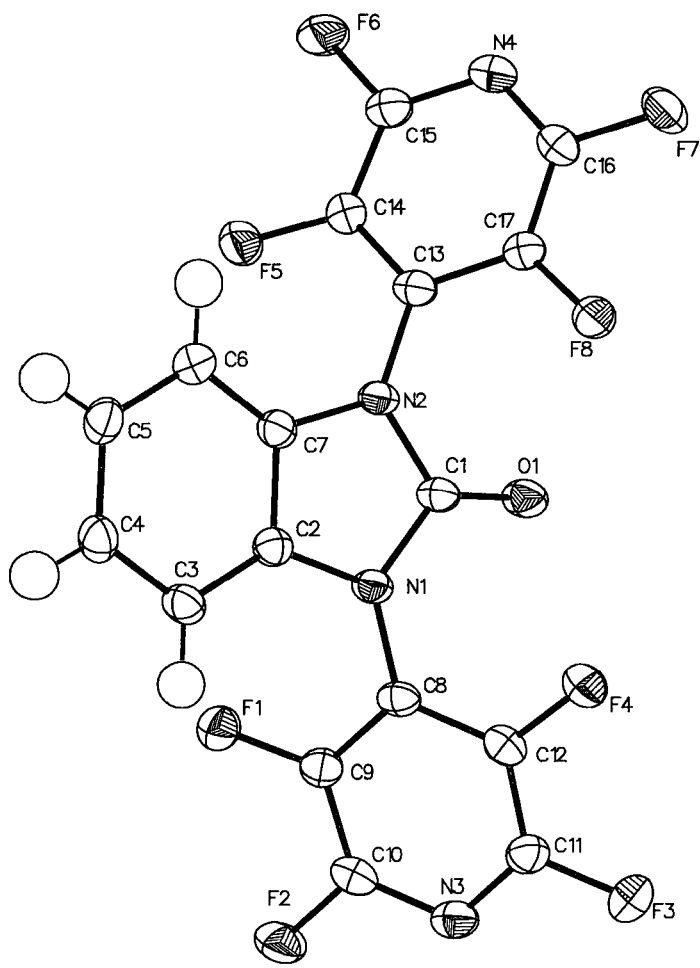
Figure 7A:
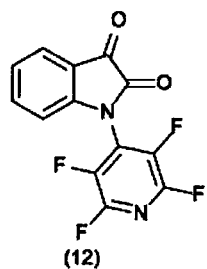
FIG. 7a shows the product (12) of the reaction of isatin (10) and pentafluoropyridine.
Figure 7B:
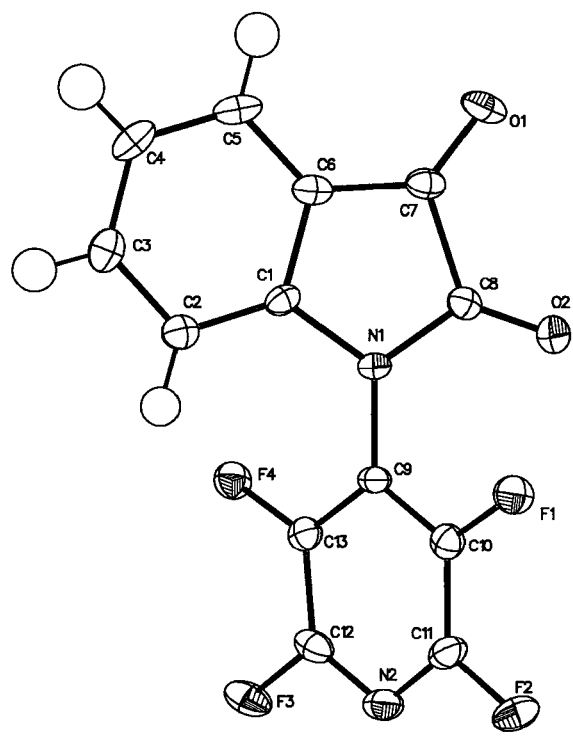
Figures 8, 9:
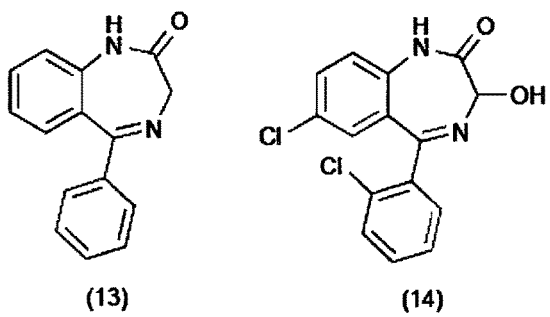
FIG. 8 shows the chemical structure of six compounds and a table showing the ¹⁹F NMR shifts for amino and amido substituted tetrafluoropyridine systems.
FIG. 9 shows the chemical structure of 1,4-benzodiazepine (13) and lorazepam (14)
Figure 11:
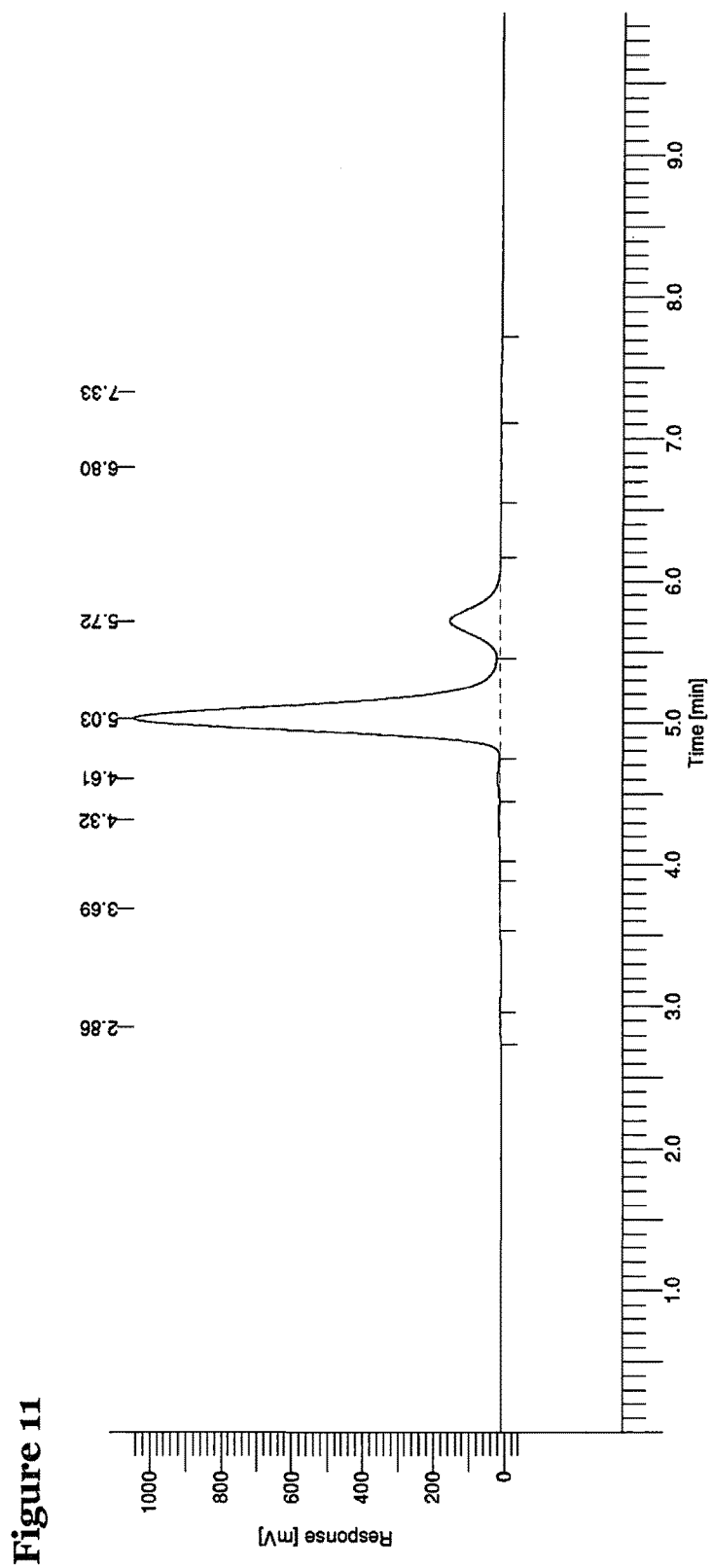
FIG. 11 is a chromatogram of the isolated R enantiomer of compound (5) at 254 nm.

As a final evaluation of the reaction, the inventors investigated the applicability of these reaction conditions to the arylation of amides in general. A range of simple amides, see FIG. 5, was treated with pentafluoropyridine under the standard conditions described above. Most of these simple amides showed little reactivity as analysed by $^{19}F$ NMR with the exception of the cyclic urea (9) and isatin (10). The chemical structure of the products (11) and (12) of the reactions of cyclic urea (9) and isatin (10) with pentafluoropyridine are shown in FIGS. 9a and 10a respectively. Although yields were lower than observed in the benzodiazepine series (52% for the reaction of cyclic urea and 64% for isatin), NMR analyses were supported by X-ray crystal structures of the products, shown in FIGS. 9b and 10b. In the case of the cyclic urea (9), no mono adduct was observed, not even when one equivalent of pentafluoropyridine was used with a 50:50 mixture of bis-adduct (11) and starting urea (9) observed after overnight stirring under these conditions.

In all of these products, $^{19}F$ NMR data was consistent, both in terms of patterns and shifts observed for the tetrafluoropyridine ring systems, whether they were connected via the four position to amide or amine nitrogens. The differing environments experienced by the ring fluorines were observable in the $^{19}F$ NMR and supported by the crystal structures. This is most noticeable for the amido substituting ring B in the bis-tetrafluoropyridine derivative (6). The 3 and 5 position fluorines show resonances at −140.78 ppm and −146.15 ppm and in the crystal structures the environments appear radically different, a consequence of hindered rotation around the pyridine amide nitrogen bond in the benzodiazepine system. The shift correlations for the variously substituted perfluorinated final products are summarized in FIG. 8.

Conclusions

A possible explanation for the surprising reactivity of the above amides with pentafluoropyridine under the mild conditions used may lie with the pKa of the amides examined in this paper. Documented[11] pKa values for benzodiazepines, admittedly in aqueous solvents, suggest figures in the region of 12.49 for the simple 1,4-benzodiazepine (13), shown in FIG. 9, and 13.0 for Lorazepam[12] (14), also shown in FIG. 9. These values, coupled with the measured value for triethylamine in dimethyl formamide[13] at 9.25, might suggest that the conditions employed herein allow sufficient deprotonation of the benzodiazepine amide to occur, thereby allowing the SNAR reaction on pentafluoropyridine to occur, albeit slowly.

This pKa dependence hypothesis has some support when the reactivity of cyclic urea (9) and isatin (10) are considered compared to the other amides shown in FIG. 4 which fail to react. The reported[14] aqueous pKas are 11.9 and 11.95 for cyclic urea (9) and isatin (10) respectively, which would suggest that some deprotonation could occur. However, the remaining amides shown in FIG. 4 are significantly less acidic. Acetanilide for example has a documented pKa value of 22.3 in dimethylformamide[15].

$^{19}F$ NMR shifts are consistent with the structures deduced by X-ray crystallography. Of particular interest is the change in pattern observed for the fluorines on the tetra-fluorine rings residing on the benzodiazepine 1-nitrogen. As previously explained, the 3 and 5 position fluorines for the bis-tetrafluoropyridine derivative (6) shows resonances at −140.78 and −146.15 ppm. In the crystal structures of these compounds the environments of the two fluorines appear radically different. Hindered rotation around the pyridine amide nitrogen bond might also be expected to occur. It is interesting, and perhaps not surprising, to note that this effect is not observed for the pyridine rings substituting the five-membered systems for the products (11) and (12) obtained from the reactions of cyclic urea (9) and isatin (10).

EXAMPLE 2: DETERMINATION OF ANTIBACTERIAL ACTIVITIES

Experimental

For each putative antimicrobial, determination of the antimicrobial susceptibility was performed in strict accordance with the recommendations of the British Society for Antimicrobial Chemotherapy. Isosensitest agar (Oxoid) was prepared according to the manufacturer's instructions and sterilized by autoclaving at 116° C. for 20 min. This was then cooled to 50° C. in a waterbath. A 10 mg sample of each antimicrobial was dissolved in 1 mL DMSO. A 256 μL aliquot was added to 19.744 mL of molten Isosensitest agar at 50° C. and mixed well. This was poured into a Petri dish to produce a culture plate containing a final concentration of 128 μg/mL. Smaller volumes of solution (ranging from 128-2 μL) were also incorporated into agar plates in similar fashion to produce a final concentration range of 128-1 μg/mL. A set of control plates was prepared containing DMSO at an identical concentration range without antimicrobial.

A panel of microorganisms was obtained from the National Collection of Type Cultures (NCTC), Colindale, UK, the National Collection of Pathogenic Fungi (NCPF), Colindale, UK, and the American Type Culture Collection (ATCC), Manassas, Va. USA. The panel included a range of pathogenic species and comprised *Bacillus subtillis, Listeria monocytogenes, Staphyloccci epidermidis, Staphylococcus aureus, Staphylococcus aureus* (MRSA) and *Streptococcis pyogenes*, all of which are Gram-positive bacteria. Each strain was cultured onto Columbia agar (Oxoid) and incubated overnight at 37° C. Colonies were then suspended in sterile distilled water (SDW) to produce a suspension of 1.5×10$^8$ colony forming units CFU/mL using a densitometer. This suspension was then diluted 1/15 in SDW and 1 μL was inoculated onto all test media using a semi-automated multipoint inoculator (final inoculum: 10 000 CFU per spot). All media were incubated at 37° C. for 24 h and examined for the presence of growth. The minimum inhibitory concentration (MIC) of each compound was recorded as the lowest concentration to completely inhibit visible growth. All tests were repeated on a separate occasion to ensure reproducibility.

Results and Discussion

The minimum inhibitory concentration of compound (5) is shown in FIG. 10.

It will be observed that 5-Phenyl-S-3-amino-2,3-dihydro-1H-1,4-benzodiazepin-2-one (5) exhibited antibacterial activity against *Listeria monocytogenes, Staphyloccci epidermidis, Staphylococcus aureus, Staphylococcus aureus* (MRSA) and *Streptococcis pyogenes* but not *Bacillus subtilis*.

EXAMPLE 3: DETERMINATION OF ANTIBACTERIAL ACTIVITIES OF THE TWO ENANTIOMERS OF 5-PHENYL-3-[(TETRAFLUOROPYRIDIN-4-YL)AMINO]-2,3-DIHYDRO-1H-1,4-BENZODIAZEPIN-2-ONE (5)

Given the antimicrobial activity of 5-Phenyl-3-[(tetrafluoropyridin-4-yl)amino]-2,3-dihydro-1H-1,4-benzodiazepin-2-one (5), it was decided to test the activity of each of the enantiomers.

Experimental

5-Phenyl-S-3-[(tetrafluoropyridin-4-yl)amino]-2,3-dihydro-1H-1,4-benzodiazepin-2-one 5-Phenyl-S-3-amino-2,3-dihydro-1H-1,4-benzodiazepin-2-one (5) (100 mg) in dimethyl formamide (1.95 ml) was treated with pentafluoropyridine (0.041 ml) and triethylamine (0.10 ml). The mixture was stirred overnight before being partitioned between ethyl acetate and water. The ethyl acetate layer was then washed with successive portions of water before being dried over sodium sulphate, decanted and concentrated in vacuo. Chromatography on silica (40% ethyl acetate in 40/60 petrol), followed by trituration with hexane gave the desired product as a white solid.

Yield: 0.039 g (28%); white solid; mp 108.5-111.4° C. $^1$H NMR (400 MHz, CDCl$_3$): δ=9.0 (s, 1H), 7.65 (m, 1H), 7.55-7.36 (m, 5H), 7.35-7.25 (m, 3H), 6.73 (d, 1H), 5.44 (d, 1H). $^{13}$C NMR (100 MHz, CDCl$_3$): δ=168.27, 168.05, 145.39, 143.03, 138.30, 136.96, 135.95, 133.00, 132.67, 131.43, 131.01, 130.47, 129.79, 128.41, 127.51, 124.69, 121.61. $^{19}$F NMR (376 MHz, CDCl$_3$) −93.59 (m, 2F), −161.83 (m, 2F). MS (EI) m/z: 401.10 [M+1]+; HRMS (ESI-TOF) m/z: [M+H]+ Calcd for C$_{20}$H$_{13}$F$_4$N$_4$O, 401.1025; Found 401.1028.

5-Phenyl-R-3-[(tetrafluoropyridin-4-yl)amino]-2,3-dihydro-1H-1,4-benzodiazepin-2-one 5-Phenyl-R-3-amino-2,3-dihydro-1H-1,4-benzodiazepin-2-one (5) (86 mg) in dimethyl formamide (1.7 ml) was treated with pentafluoropyridine (0.036 ml) and triethylamine (0.087 ml). The mixture was stirred overnight before being partitioned between ethyl acetate and water. The ethyl acetate layer was then washed with successive portions of water before being dried over sodium sulphate, decanted and concentrated in vacuo. Chromatography on silica (40% ethyl acetate in 40/60 petrol), followed by trituration with hexane gave the desired product as a white solid.

Yield: 0.03 g (22%); white solid; mp 109.4-111.5° C. $^1$H NMR (400 MHz, CDCl$^3$): δ=9.07 (s, 1H, CONH), 7.65 (m, 1H, ArH), 7.55-7.35 (m, 5H, ArH), 7.34-7.32 (m, 3H, ArH), 6.73 (d, 1H, CHNH), 5.44 (d, m). $^{13}$C NMR (100 MHz, CDCl$_3$): δ=168.22, 167.89, 145.39, 143.02, 138.31, 136.91, 135.91, 133.00, 132.66, 131.45, 131.02, 130.47, 129.78, 128.41, 127.52, 124.72, 121.69. $^{19}$F NMR (376 MHz, CDCl$_3$) −93.59 (m, 2F), −161.84 (m, 2F): MS (EI) m/z: 401.10 [M+1]+; HRMS (ESI-TOF) m/z: [M+H]+ Calcd. for C$_{20}$H$_{13}$F$_4$N$_4$O, 401.1025; Found 401.1014.

HPLC-Chiral Analysis

Samples of 5-Phenyl-R-3-[(tetrafluoropyridin-4-yl)amino]-2,3-dihydro-1H-1,4-benzodiazepin-2-one and 5-Phenyl-S-3-[(tetrafluoropyridin-4-yl)amino]-2,3-dihydro-1H-1,4-benzodiazepin-2-one were dissolved in methanol at a concentration of approx. 0.5 mg/ml.

Each sample was analysed using a PerkinElmer Series 200 HPLC equipped with a diode array detector analysing at 254 nm.

| Column | Daicel ChiralPak IA, 250 × 4.6 mm, 5 μm (P/No. 80325) equipped with guard cartridge. |
|---|---|
| Column oven | 25° C. |
| Injection volume | 10 μl |
| Flow rate | 1 ml/min |

The HPLC method used was:

| Step | Tim (minutes) | Flow (ml/min) | % Hexane | % Ethanol | % Dichloromethane |
|---|---|---|---|---|---|
| 0 | 0.5 | 1 | 70 | 15 | 15 |
| 1 | 10 | 1 | 70 | 15 | 15 |

The injector port was washed with methanol between injections.

A sample of methanol was analysed between samples to check for contamination and carry-over.

Samples were analysed in triplicate.

Figure 12:
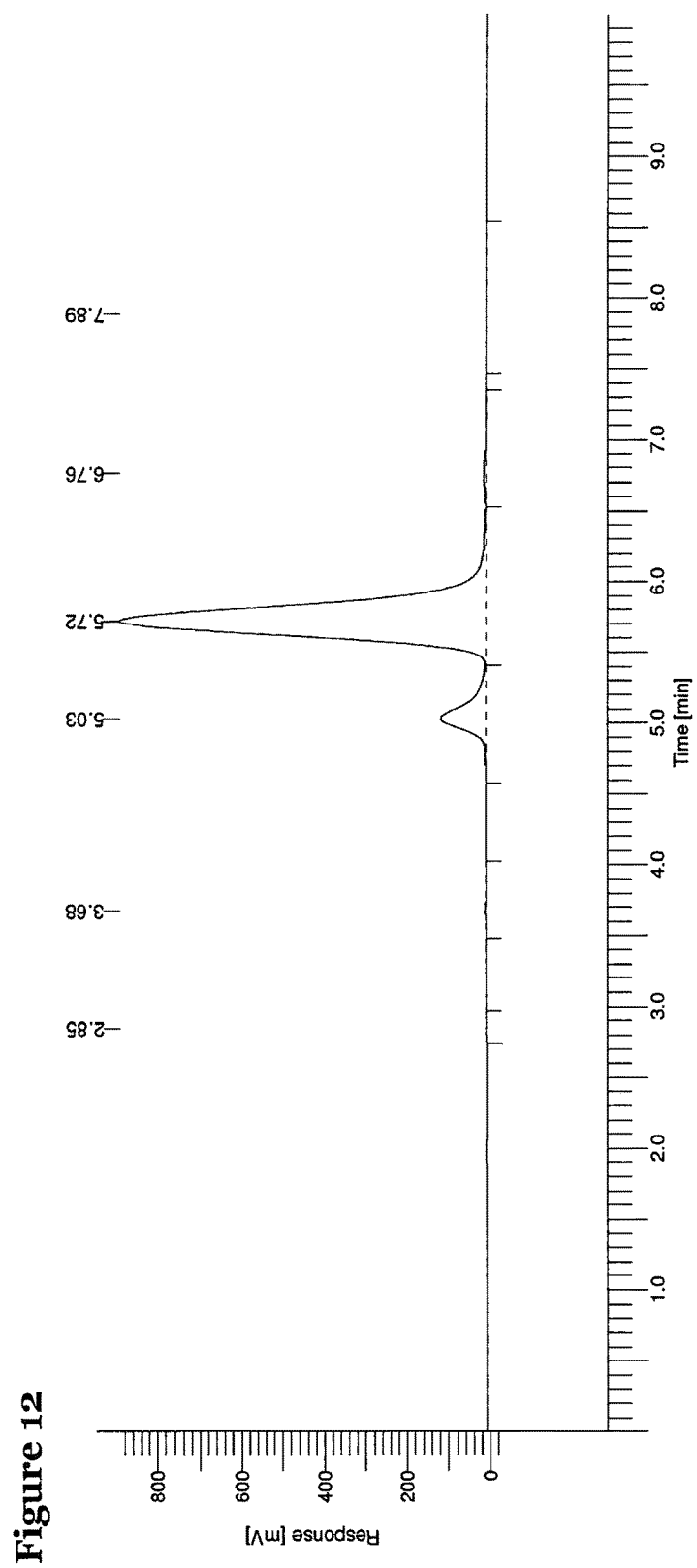
FIG. 12 is a chromatogram of the isolated S enantiomer of compound (5) at 254 nm.

A chromatogram of the sample containing the isolated R enantiomer sample recorded at 254 nm is shown in Figure ii and a chromatogram of the sample containing the isolated S enantiomer sample recorded at 254 nm is shown in FIG. 12.

It will be noted that the retention time of the R enantiomer is 5.03 minutes and the retention time of the S enantiomer is 5.72 minutes. It was calculated that the sample containing the isolated R enantiomer had an enantiomeric excess of 73% and the sample containing the isolated S enantiomer had an enantiomeric excess of 81%.

Determination of Antimicrobial Susceptibility

Determination of the antimicrobial susceptibility of the samples containing the isolated R and S enantiomers was performed as set out in Example 2.

Results and Discussion

The minimum inhibitory concentration of the two enantiomers and the racemate is shown in FIG. 13.

It will be noted that the R enantiomer was effective against *Staphyloccci epidermidis, Staphylococcus aureus* and *Staphylococcus aureus* (MRSA). Meanwhile, the S enantiomer was effective against all of the compounds which the racemate was effective against, i.e. *Listeria monocytogenes, Staphyloccci epidermidis, Staphylococcus aureus, Staphylococcus aureus* (MRSA) and *Streptococcis pyogenes*. Additionally, the S enantiomer is surprisingly also effective against *Bacillus subtilis*.

EXAMPLE 4: DETERMINATION OF ANTIVIRAL ACTIVITIES

Given the antibacterial properties of 5-Phenyl-3-amino-2,3-dihydro-1H-1,4-benzodiazepin-2-one it was decided to test the compounds to determine the compound's antiviral properties. Accordingly, 5-Phenyl-3-amino-2,3-dihydro-1H-1,4-benzodiazepin-2-one was tested to see if it was effective against Human RSV (Respiratory Syncytial Virus).

Experimental

Notes Cell obtained from ATCC and virus prep was subjected to one round of centrifugation through a 40% (V/V) glycerol to remove any interferon produced from infected cells. Growth medium was Dulbecco's modified Eagle's medium (DMEM) with 10% (v/v) foetal calf serum (FCS), Viral maintenance medium was DMEM+2% (v/v) FCS Cell Cytotoxicity—$CC_{50}$ (concentration at which 50% cell toxicity is observed):

A549 cells and HeLa cells were used to seed a set of 96 well plates grown until 50% confluent, a 2 fold serial dilution of 5-Phenyl-S-3-amino-2,3-dihydro-1H-1,4-benzodiazepin-2-one (5) was performed on each cell line with DMSO (only) as control starting with 100 µM of 5-Phenyl-S-3-amino-2,3-dihydro-1H-1,4-benzodiazepin-2-one (5). Medium used was DMEM+2% FCS (normal medium for viral growth).

Cells were allowed to grow for 6-8 days to mimic a TCID50 assay after which cell viability was determined by adding Almar blur (similar to XTT) and reading at 600 nm (excitation 540 nm). No significant difference was observed between cells treated with 5-Phenyl-S-3-amino-2,3-dihydro-1H-1,4-benzodiazepin-2-one (5) and the DMSO control. No significant difference was observed between HeLa and A549 cells.

Accordingly, CC50 for 5-Phenyl-S-3-amino-2,3-dihydro-1H-1,4-benzodiazepin-2-one (5) was greater than or equal to 100 µM. This shows that 5-Phenyl-S-3-amino-2,3-dihydro-1H-1,4-benzodiazepin-2-one (5) is not toxic at concentrations up to 100 µM.

Infected Cell Viability Assay (A549 Only)

96 wells plates were set up as previously described. As before a 2 fold serial dilution of 5-Phenyl-S-3-amino-2,3-dihydro-1H-1,4-benzodiazepin-2-one (5) was added prior to addition of virus at a multiplicity of infection (moi) of 0.1, as determined by a plaque assay, in a volume of 50 µl (starting conc 100 µM). After incubating for 4 hours RSV A2 strain was added at an moi of 0.1 maintaining the concentration of 5-Phenyl-S-3-amino-2,3-dihydro-1H-1,4-benzodiazepin-2-one (5). As before, DMSO was the control. The final lane was a mock infected minus 5-Phenyl-S-3-amino-2,3-dihydro-1H-1,4-benzodiazepin-2-one (5) to show viability of cells after 8 days incubation.

Figure 14:
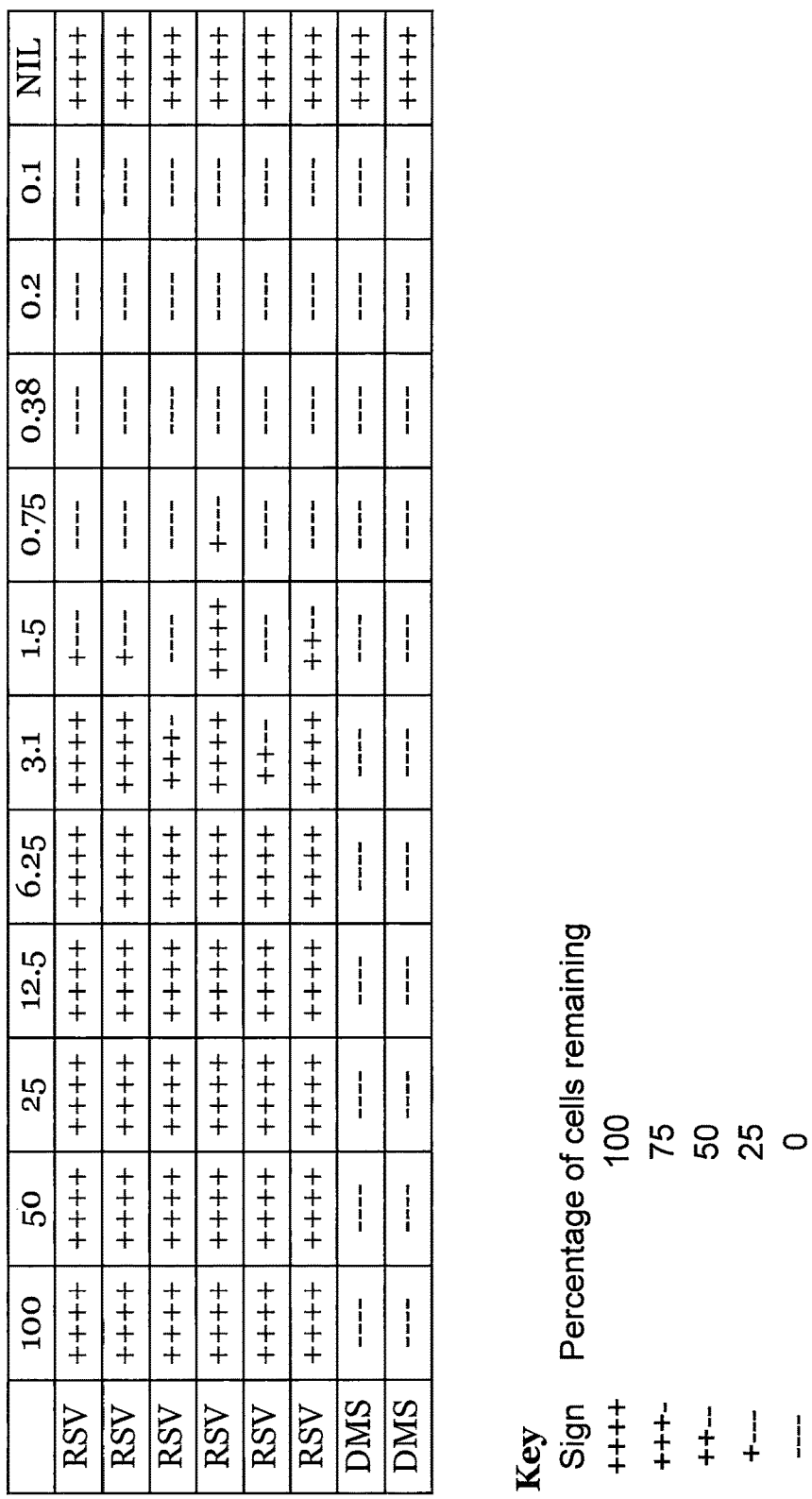
FIG. 14 is a table showing the antiviral activity of compound (5), where compound (5) was added before the virus.

Every two days for up to 8 days the media plus drug was replaced to maintain activity, after 8 days cell viability was assayed by cell staining with methylene blue. Each experiment was performed twice with similar results, see FIG. 14. A quick calculation using the statistical method of Reed and Meunch suggests a half maximal effective concentration (EC50) of 2.4 µM.

Figure 15:
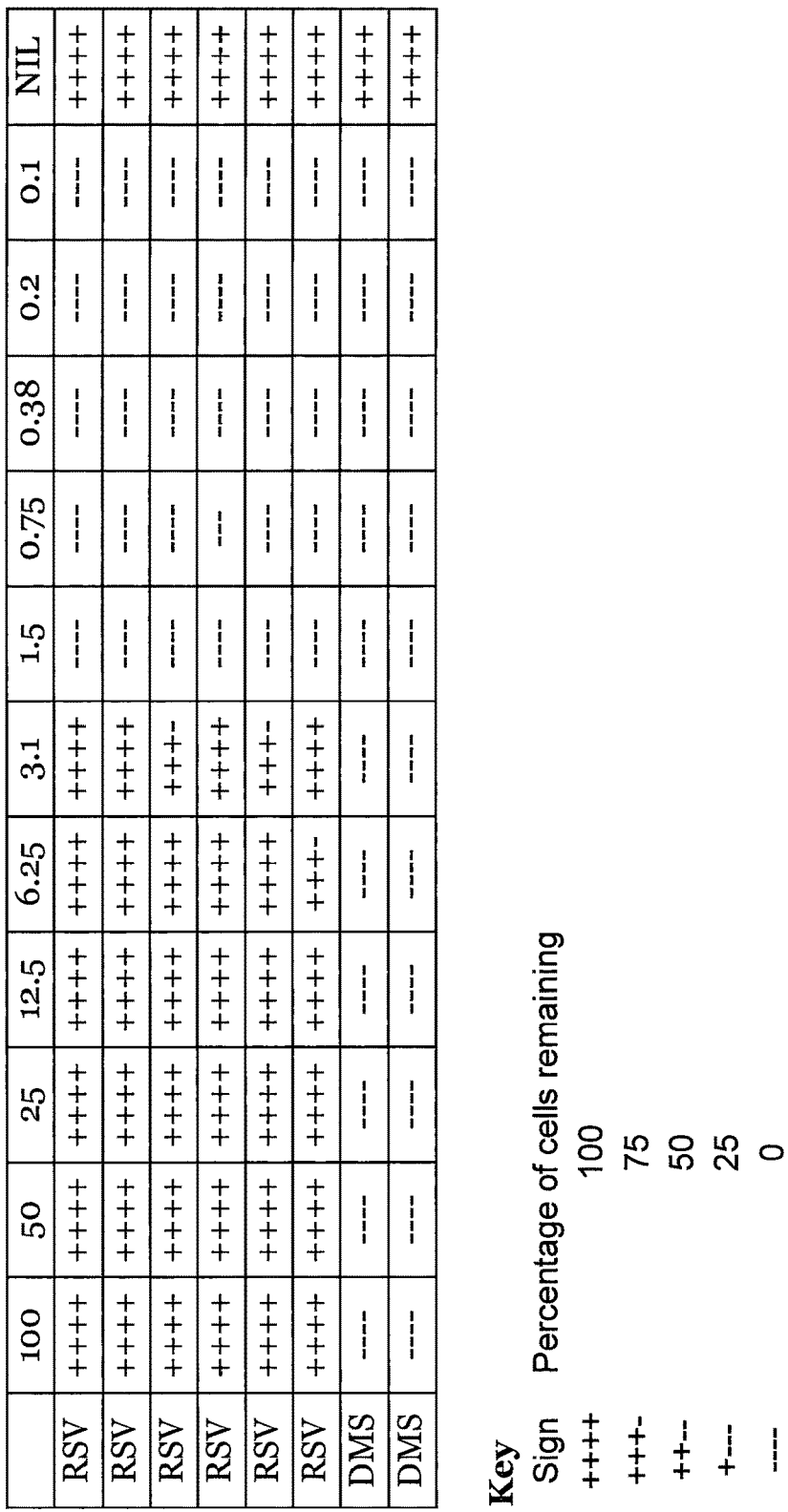
FIG. 15 is a table showing the antiviral activity of compound (5), where compound (5) was added after the virus.

An alternative experiment was set up as before except virus, at an moi of 0.1, was added before the drug and allowed to incubate for 4 hours. After incubation the media was aspirated, and replaced with 5-Phenyl-S-3-amino-2,3-dihydro-1H-1,4-benzodiazepin-2-one (5) as above. Again the plates were incubated for 8 days before assaying. The results are shown in FIG. 15.

Again, using Reed & Meunch we get an EC50 of around 3.0 µM.

Plaque Reduction Assay

A549 cells were seeded into a T25 flask and grown until 60-70% confluent. To one set of flasks (n=3) 5-Phenyl-S-3-amino-2,3-dihydro-1H-1,4-benzodiazepin-2-one (5) in DMSO was added at a concentration of 10 µM and allowed to incubate for 3-4 hours before the addition of RSV at an moi of to and incubated until extensive cytopathic effect (cpe) was evident, usually after 3 days. The concentration of 5-Phenyl-S-3-amino-2,3-dihydro-1H-1,4-benzodiazepin-2-one (5) was kept constant by replacing the medium each day (RSV is largely cell associated). After which virus was harvested by homogenising the cells in a final volume of 1 ml. The viral titre was determined by plaque assay and staining after 8 days. A control assay was conducted using DMSO in place of the DMSO solution of 5-Phenyl-S-3-amino-2,3-dihydro-1H-1,4-benzodiazepin-2-one (5).

A comparison of the control titre with that exposed to the 10 µM solution of 5-Phenyl-S-3-amino-2,3-dihydro-1H-1,4-benzodiazepin-2-one (5) indicated a drop from $4.5 \times 10^5$ viral infectivity units to $2.3 \times 10^3$ upon exposure to 5-Phenyl-S-3-amino-2,3-dihydro-1H-1,4-benzodiazepin-2-one (5).

In an analagous assay, RSV was added X hours prior to 5-Phenyl-S-3-amino-2,3-dihydro-1H-1,4-benzodiazepin-2-one (5) a similar drop was observed.

TCID50 was also performed and gave similar data.

Results and Discussion

The results show that 5-Phenyl-S-3-amino-2,3-dihydro-1H-1,4-benzodiazepin-2-one (5) is not toxic at concentrations up to 100 µM.

5-Phenyl-S-3-amino-2,3-dihydro-1H-1,4-benzodiazepin-2-one (5) was found to be an effective antiviral agent at concentrations much lower than 100 µM, with EC50 values of around 2.4 µM and 3.0 µM observed.

Additionally, exposing cells infected with RSV to 5-Phenyl-S-3-amino-2,3-dihydro-1H-1,4-benzodiazepin-2-one (5) caused a marked drop in the viral infectivity units.

Accordingly, 5-Phenyl-S-3-amino-2,3-dihydro-1H-1,4-benzodiazepin-2-one (5) shows considerable promise as an antiviral compound.

EXAMPLE 5: SYNTHESIS OF FURTHER COMPOUNDS

As set out below, the inventors synthesised further compounds which fell within the scope of the invention.

(3S)-5-phenyl-3-[(2-ethoxy-3,5,6-trifluoropyridin-4-yl)amino]-2,3-dihydro-1H-1,4-benzodiazepin-2-one

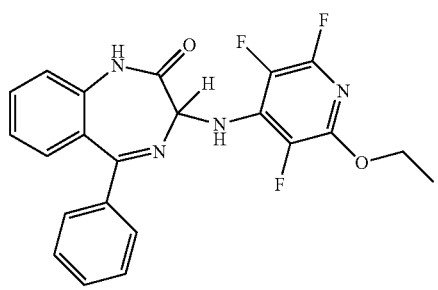 [SMILES: CCOc1nc(F)c(F)c(NC2N=C(c3ccccc3)c3ccccc3NC2=O)c1F]

(3S)-5-phenyl-3-[(tetrafluoropyridin-4-yl)amino]-2,3-dihydro-1H-1,4-benzodiazepin-2-one (145 mg, 0.36,mmoles) was dissolved in ethanol (3 ml) and treated with sodium ethoxide (0.26 ml of a 2.8 M solution, 0.72 mmoles). The mixture was heated to 75° C. for 6.5 hours. Ethanol was removed in vacuo and the residue taken up in ethyl acetate and washed with water. The ethyl acetate layer was dried over sodium sulphate, filtered and concentrated in vacuo. Chromatography on silica in 200/8/1 dicloromethane, ethanol, ammonia gave the title compound as a white solid.

Yield: 0.105 g (0.24 mmoles, 67%); $^1$H NMR (400 MHz, CDCl$_3$): δ=9.61 (s, 1H, CONH), 7.64-7.25 (m, 9H, ArH), 6.47 (bd, 1H, CHNH), 5.41 (d, 1H, CHNH), 4.38 (2H, q, CH$_3$CH$_2$), 1.41 (3H, t, CH$_2$CH$_3$). $^{13}$C NMR (100 MHz, CDCl$_3$): δ=168.64, 167.91, 145.77, 143.5, 138.52, 137.16, 134.1, 133.97, 132.47, 131.84, 131.35, 130.79, 129.85, 128.30, 127.54, 124.43, 121.60, 70.36, 62.92, 14.55: $^{19}$F (376 MHz, CDCl$_3$) −96.18 (m, 1F), −162.39 (m, 1F), −168.60 (1F, m): MS (EI) m/z: 428.9 [M+1]+; retention time 3.84 minutes.

(3S)-5-phenyl-3-[(2,3,6-trifluoro-6-(methylsulphanyl) pyridin-4-yl)amino]-2,3-dihydro-1H-1,4-benzodiazepin-2-one

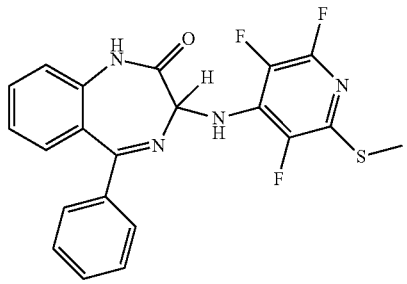 [SMILES: CSc1nc(F)c(F)c(NC2N=C(c3ccccc3)c3ccccc3NC2=O)c1F]

(3S)-5-phenyl-3-[(tetrafluoropyridin-4-yl)amino]-2,3-dihydro-1H-1,4-benzodiazepin-2-one (75 mg, 0.19 mmoles) was dissolved in dimethylformamide (3 ml) and treated with sodium thiomethoxide (52 mg, 0.8 mmoles). The mixture was heated to 80° C. for 6.5 hours. The residue was taken up in ethyl acetate and washed with water (×5). The ethyl acetate layer was dried over sodium sulphate, filtered and concentrated in vacuo. Chromatography on silica in 200/8/1 dicloromethane, ethanol, ammonia gave the title compound as a white solid.

Yield: 0.078 g (0.182 mmoles, 96%); $^1$H NMR (400 MHz, CDCl$_3$): δ=9.00 (s, 1H, CONH), 7.61 (m, 1H), 7.51-7.30 (m, 5H, ArH), 7.33-7.25 (3H, m, ArH), 6.47 (bd, 1H, CHNH), 5.41 (d, 1H, CHNH), 2.54 (3H, s, CH$_3$S): $^{19}$F (376 MHz, CDCl$_3$) −92.12 (m, 1F), −142.2 (m, 1F), −164.20 (1F, m): MS (EI) m/z: 429 [M+1]+; retention time 3.87 minutes.

(3S)-5-phenyl-3-[(2,3,6-trifluoro-6-methylsulphonyl pyridin-4-yl)amino]-2,3-dihydro-1H-1,4-benzodiazepin-2-one

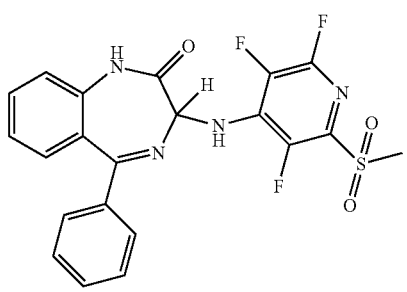 [SMILES: CS(=O)(=O)c1nc(F)c(F)c(NC2N=C(c3ccccc3)c3ccccc3NC2=O)c1F]

(3S)-5-phenyl-3-[(2,3,6-trifluoro-6-(methylsulphanyl) pyridin-4-yl)amino]-2,3-dihydro-1H-1,4-benzodiazepin-2-one (78 mg, 0.182 mmoles) was dissolved in methanol/water (4 ml, 3:1) and treated with oxone (240 mg). After 5 days at room temperature, the residue was taken up in ethyl acetate and washed with water (×5). The ethyl acetate layer was dried over sodium sulphate, filtered and concentrated in vacuo. Chromatography on silica in 200/8/1 dicloromethane, ethanol, ammonia gave the title compound as a white solid.

Yield: 0.045 g (0.097 mmoles, 54%); $^1$H NMR (400 MHz, CDCl$_3$): δ=10.88 (s, 1H, CONH), 7.41-7.15 (m, 9H, ArH), 6.85 (bd, 1H, CHNH), 5.14 (d, 1H, CHNH), 3.14 (3H, s, CH$_3$SO$_2$): $^{19}$F (376 MHz, CDCl$_3$) −88.48 (m, 1F), −137.50 (m, 1F), −150.87 (1F,m): MS (EI) m/z: 459.7 [M−1]$^-$; retention time 2.64 minutes.

(3S)-5-phenyl-3-[(2,3,6-trifluoro-6-(morpholin-4-yl) pyridin-4-yl)amino]-2,3-dihydro-1H-1,4-benzodiazepin-2-one

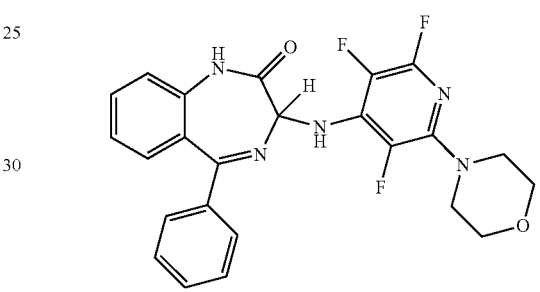

(3S)-5-phenyl-3-[(tetrafluoropyridin-4-yl)amino]-2,3-dihydro-1H-1,4-benzodiazepin-2-one (90 mg, 0.22 mmoles) was dissolved in dimethylformamide (0.5 ml) and treated with morpholine (87 mg, 0.24 mmoles) and potassium carbonate (68 mg, 0.49 mmoles). The mixture was heated to 1000 C for 12 hours. The residue was taken up in ethyl acetate and washed with water (×5). The ethyl acetate layer was dried over sodium sulphate, filtered and concentrated in vacuo. Chromatography on silica in 25-50% ethylacetate in hexane gave the title compound as a pale yellow solid.

Yield: 0.04 g (0.085 mmoles, 39%); $^1$H NMR (400 MHz, CDCl$_3$): δ=9.00 (s, 1H, CONH), 7.61 (m, 1H), 7.51-7.30 (m, 5H, ArH), 7.33-7.25 (3H, m, ArH), 6.47 (bd, 1H, CHNH), 5.41 (d, 1H, CHNH), 2.54 (3H, s, CH$_3$S): $^{19}$F (376 MHz, CDCl$_3$) −92.12 (m, 1F), −142.2 (m, 1F), −164.20 (1F,m): MS (EI) m/z: 466 [M−1]$^-$; retention time 3.18 minutes.

SUMMARY

The inventors have synthesised a number of novel compounds which comprise one or more fluorinated pyridine fragment and a benzodiazepine amine fragment.

While synthesising the compounds they were surprised to obtain products that initially comprised two fluorinated pyridine fragments. However, they were able to then successfully synthesis a compound containing only one fluorinated pyridine fragment. The inventors were surprised to observe that the mono-substituted product was surprisingly effective as an antimicrobial agent, showing both antibacterial and antiviral activity.

REFERENCES

1. P. Jeschke, Chem Bio Chem., 2004, 5, 570
2. P. Maienfisch, R. G. Hall, Chimica., 2004, 58, 93.
3. W. K. Hagmann, Journal of Medicinal Chemistry, 2008, 51, 4359.
4. J. Wang, M. Sanchez-Rosello', J. L. Acen' a, C. del Pozo, E. Sorochinsky, S. Fustero, V. A. Soloshonok and H. Liu, Chemical Reviews. 2013, 114, 2432.
5. E. A. Henderson, D. G. Alber, R. C. Baxter, S. K. Bithell, J. Budworth, M. C. Carter, A. Chubb, G. S. Cockerill, V. C. L. Dowdell, I. J. Fraser, R. A. Harris, S. J. Keegan, R. D. Kelsey, J. A. Lumley, J. N. Stables, N. Weerasekera, L. J. Wilson, K. L. Powell, Journal of Medicinal Chemistry 2007, 50, 1685.
   J. Chapman, E. Abbott, D. G. Alber, R. C. Baxter, S. K. Bithell, E. A. Henderson, M. C. Carter, A. Chubb, G. S. Cockerill, P. L. Collins, V. C. L. Dowdell, S. J. Keegan, R. D. Kelsey, M. J. Lockyer, C. Luongo, P. Najarro, R. J. Pickles, M. Simmonds, D. Taylor, S, Tims, L. J. Wilson and K. L. Powell Antimicrobial Agents and Chemotherapy (2007), 51(9), 3346-3353.
   H. Dennison, J. Warne, K. Spencer, G. Cockerill, and J. Lumley. PCT Int. Appl. 2007, WO 2007034127 A1 20070329
6. G. M. Brooke, Journal of Fluorine Chemistry 1997, 86, 1
   A. S. Hudson A S, A. Hoose, C. R Coxon, G. Sandford and S. L. Cobb, Tetrahedron Letters 2013, 54, 4865
7. J. Wielgat and Z. Domagala. Polish Journal of Chemistry. 1978, 53, 2349-2354
8. W. Rasshoffer and F. Vogtle, Tetrahedron Letters. 1979, 14, 1217
9. V. V Litvak, I. Y Mainagashev and O. G. Bukhanets, Nucleosides, Nucleotides and Nucleic Acids, 2005, 24, 1373
10. M. C. Carter, D. G. Alber, R. C. Baxter, S. K. Bithell, J. Budworth, A. Chubb, G. S. Cockerill, V. C. L. Dowdell, E. A. Henderson, S. J. Keegan, R. D. Kelsey, M. J. Lockyer, J. N. Stables, L. J. Wilson and K. L. Powell. Journal of Medicinal Chemistry, 2006, 49, 2311.
11. P. Seller and I. Zimmerman, Arzneimittel-Forschung, 1983, 33, 1519
12. Prescribing Information Brochure 7N17, Searle Laboratories, Chicago, Ill., (August) 1977.
13. I. M. Kolthoff, M. K. Chantooni, H. Smagowski, Analytical Chemistry, 1970, 42, 1622. K. Izutsu, T. Nakamura, K. Takizawa, A. Takeda, Bulletin of the Chemical Society of Japan, 1985, 58, 455. E. Roletto, A. Vanni, Talanta, 1977, 24, 73.
14. D. J. Brown, Journal of the Chemical Society, 1958, 1974. L. A. Casey, R. Galt and M. A. Page, Journal of the Chemical Society, Perkin Transactions 2, Physical Organic Chemistry, 1993, 1, 23.
15. F. Maran, D. Celadon, M. G. Severin, E. Vianello, Journal of the American Chemical Society, 1991, 113, 9320.
16. K. E. Schwiebert, D. N. Chin, J. C. MacDonald and G. M. Whitesides, Journal of the American Chemical Society, 1996, 118, 4018
17. O. V. Dolomanov, L. J. Bourhis, R. J. Gildea, J. A. K. Howard, H. Puschmann, J. Appl. Crystallogr. 2009, 42, 339-341.

Accordingly, the mono-substituted compound, and derivatives thereof, can be used as an effective antimicrobial agent.

The invention claimed is:

1. A compound of formula (I):

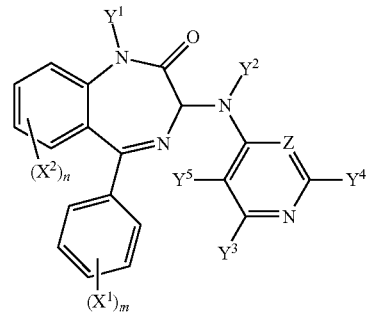

Formula (I)

wherein m is 0, 1, 2, 3, 4 or 5;
n is 0, 1, 2, 3 or 4;
$X^1$ is a $C_{1-5}$ straight or branched alkyl or alkenyl, or a halogen;
$X^2$ is a $C_{1-5}$ straight or branched alkyl or alkenyl, or a halogen;
$Y^1$ is H or a $C_{1-5}$ straight or branched alkyl or alkenyl;
$Y^2$ is H or a $C_{1-5}$ straight or branched alkyl or alkenyl;
$Y^3$ is F, $R^1$, $NR^1R^{1'}$, $OR^1$, $SR^1$, or $SO_2R^1$;
$Y^4$ is F, $R^2$, $NR^2R^{2'}$, $OR^2$, $SR^2$, or $SO_2R^2$;
$Y^5$ is F, $R^3$, $NR^3R^{3'}$, $OR^3$, $SR^3$, or $SO_2R^3$;
Z is N or $CY^6$;
$Y^6$ is F, $R^4$, $NR^4R^{4'}$, $OR^4$, $SR^4$, or $SO_2R^4$; and
$R^1$, $R^{1'}$, $R^2$, $R^{2'}$, $R^3$, $R^{3'}$, $R^4$, and $R^{4'}$ are independently selected from the group consisting of: hydrogen, a $C_{1-5}$ straight or branched alkyl or alkenyl, $C_{3-6}$ cycloalkyl, phenyl, pyridyl, pyrimidyl, furanyl, imidazolyl, piperidinyl, morpholinyl, pyrrolidinyl, thiomorpholinyl, thiomorpholinyl S,S dioxide, $C_{2-4}$ methane sulphonyl alkyl, and $C_{2-4}$ dialkylaminoalkyl, and/or $R^1$ and $R^{1'}$ together with the nitrogen atom to which they are attached, $R^2$ and $R^{2'}$ together with the nitrogen atom to which they are attached, $R^3$ and $R^{3'}$ together with the nitrogen atom to which they are attached, and $R^4$ and $R^{4'}$ together with the nitrogen atom to which they are attached independently form pyrrolidine, piperidine, piperazine, morpholine, thiomorpholine or thiomorpholine S,S dioxide;
wherein at least one of $Y^3$, $Y^4$ and $Y^5$ is F and/or Z is CF;
or a pharmaceutically acceptable salt or solvate thereof.

2. A method of treating or ameliorating a bacterial infection or a respiratory syncytial virus (RSV) infection, the method comprising administering, to a subject in need of such treatment, a therapeutically effective amount of a compound of formula (I):

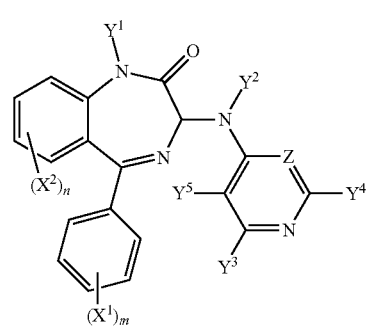

Formula (I)

wherein m is 0, 1, 2, 3, 4 or 5;

n is 0, 1, 2, 3 or 4;

$X^1$ is a $C_{1-5}$ straight or branched alkyl or alkenyl, or a halogen;

$X^2$ is a $C_{1-5}$ straight or branched alkyl or alkenyl, or a halogen;

$Y^1$ is H or a $C_{1-5}$ straight or branched alkyl or alkenyl;

$Y^2$ is H or a $C_{1-5}$ straight or branched alkyl or alkenyl;

$Y^3$ is F, $R^1$, $NR^1R^{1'}$, $OR^1$, $SR^1$, or $SO_2R^1$;

$Y^4$ is F, $R^2$, $NR^2R^{2'}$, $OR^2$, $SR^2$, or $SO_2R^2$;

$Y^5$ is F, $R^3$, $NR^3R^{3'}$, $OR^3$, $SR^3$, or $SO_2R^3$;

Z is N or $CY^6$;

$Y^6$ is F, $R^4$, $NR^4R^{4'}$, $OR^4$, $SR^4$, or $SO_2R^4$; and $R^1$, $R^{1'}$, $R^2$, $R^{2'}$, $R^3$, $R^{3'}$, $R^4$, and $R^{4'}$ are independently selected from the group consisting of: hydrogen, a $C_{1-5}$ straight or branched alkyl or alkenyl, $C_{3-6}$ cycloalkyl, phenyl, pyridyl, pyrimidyl, furanyl, imidazolyl, piperidinyl, morpholinyl, pyrrolidinyl, thiomorpholinyl, thiomorpholinyl S,S dioxide, $C_{2-4}$ methane sulphonyl alkyl, and $C_{2-4}$ dialkylaminoalkyl, and/or $R^1$ and $R^{1'}$ together with the nitrogen atom to which they are attached, $R^2$ and $R^{2'}$ together with the nitrogen atom to which they are attached, $R^3$ and $R^{3'}$ together with the nitrogen atom to which they are attached, and $R^4$ and $R^{4'}$ together with the nitrogen atom to which they are attached independently form pyrrolidine, piperidine, piperazine, morpholine, thiomorpholine or thiomorpholine S,S dioxide;

wherein at least one of $Y^3$, $Y^4$ and $Y^5$ is F and/or Z is CF;

or a pharmaceutically acceptable salt or solvate thereof.

3. The method according to claim 2, wherein the bacterial infection comprises a gram-positive bacterial infection.

4. The compound according to claim 1, wherein the $C_{3-6}$ cycloalkyl is cyclohexyl.

5. The compound according to claim 1, wherein Z is $CY^6$ and the compound has a formula (Ib):

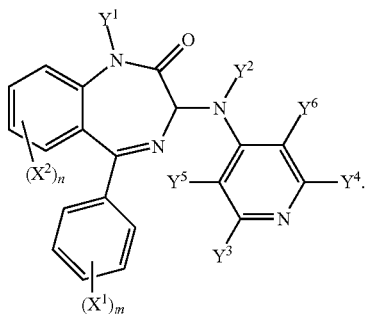

Formula (Ib)

6. The compound according to claim 1, wherein $Y^3$ is F, $Y^4$ is F, $Y^5$ is F, Z is $CY^6$, $Y^6$ is F, and the compound has a formula (Id):

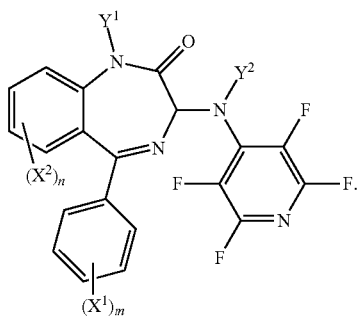

Formula (Id)

7. The compound according to claim 1, wherein both $Y^1$ and $Y^2$ are hydrogen and the compound has a formula (If):

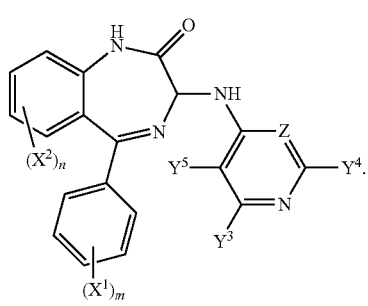

Formula (If)

8. The compound according to claim 1, wherein the compound has an S chiral centre and a formula (Ig):

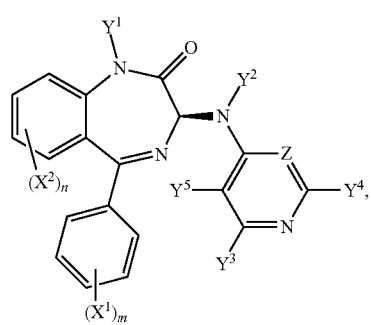

Formula (Ig)

or wherein the compound has an R chiral centre and a formula (Ih):

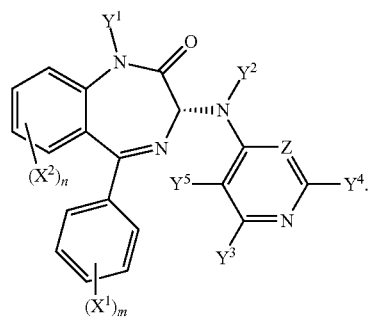

Formula (Ih)

9. The compound according to claim 1, wherein m is 0; n is 0; $Y^1$ is H; $Y^2$ is H; $Y^3$ is F; $Y^4$ is F; $Y^5$ is F; Z is CF and the compound has formula (Ij):

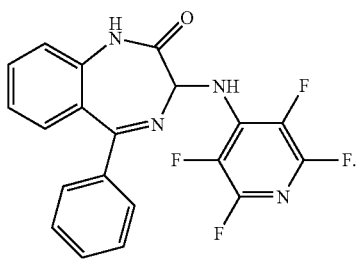

Formula (Ij)

10. The compound according to claim 9, wherein the compound has an S chiral centre and is a compound of formula (Ik):

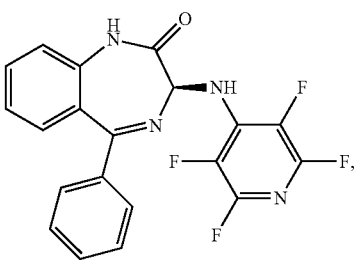

Formula (Ik)

or
wherein the compound has an R chiral centre and is a compound of formula (Il):

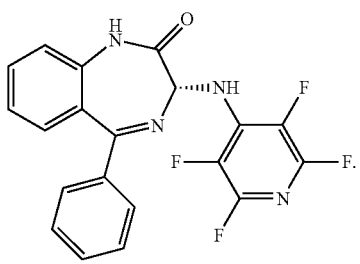

Formula (Il)

11. The compound according to claim 1, wherein the compound is a compound of formula (Im), formula (In), formula (Io), formula (Ip), formula (Iq) or formula (Ir):

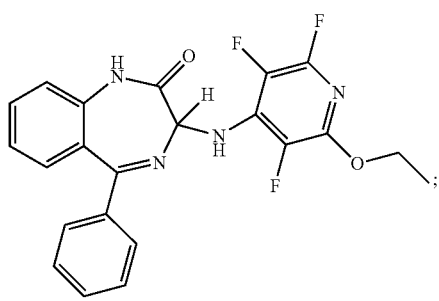

Formula (Im)

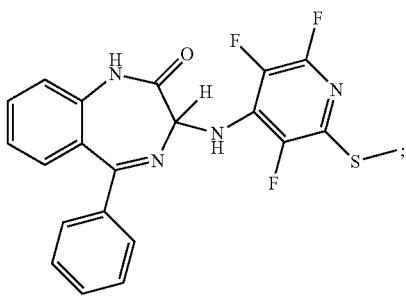

Formula (In)

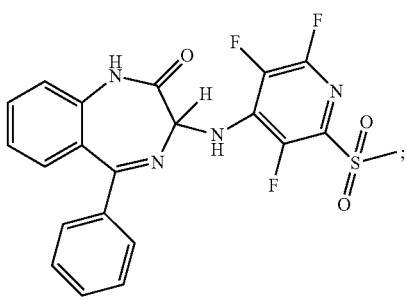

Formula (Io)

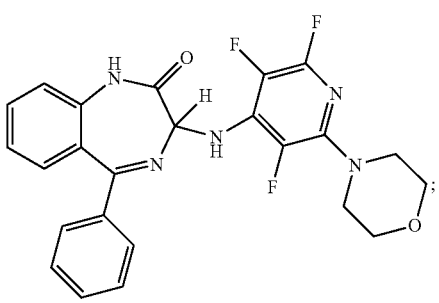

Formula (Ip)

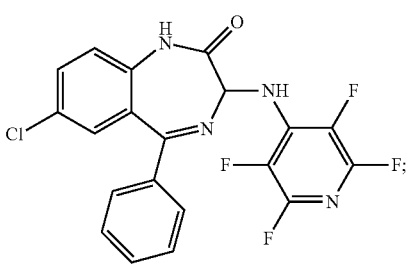

Formula (Iq)

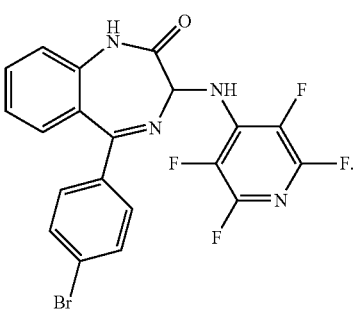

Formula (Ir)

12. A pharmaceutical composition comprising a compound according to claim 1, or a pharmaceutically acceptable salt or solvate thereof, and a pharmaceutically acceptable vehicle.

13. A method of manufacturing the compound of claim 1, the method comprising contacting an amide with a fluorinated heteroaromatic compound to provide the compound of claim 1, wherein the amide is 3-amino-5-phenyl-2,3-dihydro-1H-1,4-benzodiazepin-2-one and the fluorinated heteroaromatic compound is selected from the group consisting of a fluorinated pyridine and a fluorinated 1,3-diazine, characterised in that the method uses a ratio of less than 3:1 amide: fluorinated heteroaromatic compound.

14. The method according to claim 13, wherein the ratio of amide:fluorinated heteroaromatic compound is about 1:1.

15. The method according to claim 13, wherein the reaction is carried out in a solution comprising dimethylformamide (DMF), tetrahydrofuran (THF) and/or acetonitrile.

16. The method according to claim 13, wherein the fluorinated heteroaromatic compound is pentafluoropyridine.

\* \* \* \* \*